(12) United States Patent
Chickmath et al.

(10) Patent No.: US 10,561,615 B2
(45) Date of Patent: Feb. 18, 2020

(54) TESTOSTERONE UNDECANOATE COMPOSITIONS

(71) Applicant: Lipocine Inc., Salt Lake City, UT (US)

(72) Inventors: Basawaraj Chickmath, Plymouth, MN (US); Chandrashekar Giliyar, North Maple Grove, MN (US); Nachiappan Chidambaram, Sandy, UT (US); Mahesh Patel, Salt Lake City, UT (US); Srinivasan Venkateshwaran, Salt Lake City, UT (US)

(73) Assignee: Lipocine Inc., Salt Lake City, UT (US)

( * ) Notice: Subject to any disclaimer, the term of this patent is extended or adjusted under 35 U.S.C. 154(b) by 63 days.

(21) Appl. No.: 14/500,498

(22) Filed: Sep. 29, 2014

(65) Prior Publication Data

US 2015/0018324 A1 Jan. 15, 2015

Related U.S. Application Data

(63) Continuation of application No. 12/965,703, filed on Dec. 10, 2010, now abandoned.

(51) Int. Cl.
| | |
|---|---|
| *A61K 9/20* | (2006.01) |
| *A61K 31/568* | (2006.01) |
| *A61K 47/10* | (2017.01) |
| *A61K 47/36* | (2006.01) |
| *A61K 9/14* | (2006.01) |
| *A61K 9/16* | (2006.01) |
| *A61K 9/28* | (2006.01) |
| *A61K 9/48* | (2006.01) |
| *A61K 47/40* | (2006.01) |
| *A61K 47/38* | (2006.01) |

(52) U.S. Cl.
CPC ............ *A61K 9/2031* (2013.01); *A61K 9/146* (2013.01); *A61K 9/148* (2013.01); *A61K 9/1652* (2013.01); *A61K 9/1676* (2013.01); *A61K 9/1694* (2013.01); *A61K 9/205* (2013.01); *A61K 9/2013* (2013.01); *A61K 9/2018* (2013.01); *A61K 9/2054* (2013.01); *A61K 9/282* (2013.01); *A61K 9/286* (2013.01); *A61K 9/2853* (2013.01); *A61K 9/2866* (2013.01); *A61K 9/4866* (2013.01); *A61K 9/4875* (2013.01); *A61K 31/568* (2013.01); *A61K 47/10* (2013.01); *A61K 47/36* (2013.01); *A61K 47/38* (2013.01); *A61K 47/40* (2013.01); *A61K 9/14* (2013.01)

(58) Field of Classification Search
None
See application file for complete search history.

(56) References Cited

U.S. PATENT DOCUMENTS

| | | | |
|---|---|---|---|
| 2,680,749 A | 5/1954 | Cawley et al. |
| 2,742,487 A | 4/1956 | Robledano |
| 3,097,139 A | 7/1963 | Sonne |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | van der Vies |
| 4,147,783 A | 4/1979 | Van der Vies |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | Van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,658,944 A | 4/1987 | Kogure et al. |
| 4,689,333 A | 8/1987 | Nohara et al. |

(Continued)

FOREIGN PATENT DOCUMENTS

| | | |
|---|---|---|
| CA | 2295028 | 1/1999 |
| CA | 2302735 | 1/2000 |

(Continued)

OTHER PUBLICATIONS

Aveed, "testosterone undecanoate", [retrieved on Mar. 23, 2015 from on-line website (http://www.drugdevelopment-technology.com/projects/aveed-testosterone-undecanoate-treatment-men-hypogonadism/)].*
U.S. Appl. No. 14/298,031, filed Jun. 6, 2014; Chandrashekar Giliyar; Office Action dated Sep. 21, 2015.
U.S. Appl. No. 14/298,768, filed Jun. 6, 2014; Chandrashekar Giliyar; Office Action dated Sep. 28, 2015.
U.S. Appl. No. 14/691,229, filed Apr. 20, 2015; Chandrashekar Giliyar; Notice of Allowance dated Sep. 29, 2015.
U.S. Appl. No. 12/965,703, filed Dec. 10, 2010; Basawaraj Chickmath; Office Action dated Oct. 22, 2015.

(Continued)

*Primary Examiner* — Kyung S Chang
(74) *Attorney, Agent, or Firm* — Thorpe North and Western, LLP; David W. Osborne

(57) ABSTRACT

The present disclosure is drawn to pharmaceutical compositions and oral dosage forms containing testosterone undecanoate, as well as related methods of treatment. In one embodiment, the oral dosage form can include a therapeutically effective amount of testosterone undecanoate and a pharmaceutically acceptable carrier. The dosage form can be formulated such that, when measured using a USP Type II apparatus in 1000 mL of 8 wt % Triton X-100 in water at 37° C. and 100 rpm, the oral dosage form releases at least 20% more testosterone undecanoate after the first 120 minutes than an equivalent dose testosterone undecanoate containing oral dosage form without the pharmaceutically acceptable carrier.

21 Claims, No Drawings

(56) References Cited

U.S. PATENT DOCUMENTS

| | | |
|---|---|---|
| 4,695,450 A | 9/1987 | Bauer |
| 4,703,042 A | 10/1987 | Bodor |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |
| 4,874,795 A | 10/1989 | Yesair |
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |
| 4,994,439 A | 2/1991 | Longenecker et al. |
| 5,014,656 A | 5/1991 | Leptich et al. |
| 5,023,108 A | 6/1991 | Bagaria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald et al. |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,120,710 A | 6/1992 | Liedtke |
| 5,140,021 A | 8/1992 | Maxson et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List et al. |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gilis |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,906,987 A * | 5/1999 | Chwalisz et al. ............ 514/177 |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahashi et al. |
| 5,962,014 A | 10/1999 | Hauer et al. |
| 5,962,017 A | 10/1999 | Hauer et al. |
| 5,965,161 A | 10/1999 | Oshlack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamme et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |

(56) References Cited

U.S. PATENT DOCUMENTS

| | | |
|---|---|---|
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder |
| 6,328,994 B1 | 12/2001 | Shimizu et al. |
| 6,340,471 B1 | 1/2002 | Kershman et al. |
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Poppe |
| 6,667,048 B1 | 12/2003 | Lambert et al. |
| 6,692,766 B1 | 2/2004 | Rubinstein et al. |
| 6,696,482 B2 | 2/2004 | Schenoy et al. |
| 6,720,001 B2 | 5/2004 | Chen et al. |
| 6,737,082 B1 | 5/2004 | Picornell Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,923,988 B2 | 5/2005 | Patel et al. |
| 6,913,244 B1 | 7/2005 | Atkinson et al. |
| 6,977,083 B1 * | 12/2005 | Huebler et al. ............... 424/434 |
| 6,982,281 B1 | 1/2006 | Chen et al. |
| 7,025,979 B2 | 4/2006 | Nieschlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 4/2012 | Dudley et al. |
| 8,338,395 B2 | 12/2012 | Hubler et al. |
| 8,778,922 B2 | 7/2014 | Giliyar et al. |
| 8,865,695 B2 | 10/2014 | Giliyar et al. |
| 9,034,858 B2 | 5/2015 | Giliyar et al. |
| 9,205,057 B2 | 12/2015 | Gilliyar et al. |
| 9,358,241 B2 | 6/2016 | Giliyar et al. |
| 9,480,690 B2 | 11/2016 | Giliyar et al. |
| 9,757,390 B2 | 9/2017 | Gilivar et al. |
| 9,943,527 B2 | 4/2018 | Gilivar et al. |
| 9,949,985 B2 | 4/2018 | Gilivar et al. |
| 10,226,473 B2 | 3/2019 | Gilivar et al. |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwartz |
| 2002/0103139 A1 | 8/2002 | Weisspapir et al. |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0127476 A1 | 7/2004 | Kershman et al. |
| 2005/0031693 A1 | 2/2005 | Babcock et al. |
| 2005/0032762 A1 | 2/2005 | Hubler et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | Nijs De et al. |
| 2005/0287212 A1 | 12/2005 | Dong et al. |
| 2006/0003002 A1 * | 1/2006 | Fikstad et al. ............... 424/468 |
| 2006/0034937 A1 * | 2/2006 | Patel ............................ 424/497 |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2009/0074859 A1 | 3/2009 | Patel |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1 | 7/2010 | Giliyar et al. |
| 2011/0039814 A1 | 2/2011 | Huatan et al. |
| 2011/0142945 A1 | 6/2011 | Chen et al. |
| 2011/0160168 A1 | 6/2011 | Dhingra |
| 2011/0251167 A1 | 10/2011 | Dudley et al. |
| 2012/0135074 A1 | 5/2012 | Chandrashekar |
| 2012/0148675 A1 | 6/2012 | Chickmath et al. |
| 2012/0244215 A1 | 9/2012 | Giliyar et al. |
| 2012/0322780 A1 | 12/2012 | Gillyar et al. |
| 2013/0023505 A1 | 1/2013 | Garfield et al. |
| 2013/0052263 A1 | 2/2013 | Fikstad et al. |
| 2013/0225544 A1 | 8/2013 | Nacheagari et al. |
| 2014/0178466 A1 | 6/2014 | Gillyar et al. |
| 2014/0179652 A1 | 6/2014 | Gillyar et al. |
| 2014/0303130 A1 | 10/2014 | Giliyar et al. |
| 2015/0064243 A1 | 3/2015 | Chen et al. |
| 2015/0038475 A1 | 5/2015 | Chickmath et al. |
| 2015/0224059 A1 | 8/2015 | Gillyar |
| 2015/0273067 A1 | 10/2015 | Patel |
| 2017/0007622 A1 | 1/2017 | Giliyar et al. |
| 2018/0125857 A1 | 5/2018 | Giliyar et al. |
| 2018/0228816 A1 | 8/2018 | Giliyar et al. |
| 2018/0228817 A1 | 8/2018 | Giliyar et al. |
| 2018/0243320 A1 | 8/2018 | Giliyar et al. |
| 2019/0125760 A1 | 5/2019 | Giliyar et al. |

FOREIGN PATENT DOCUMENTS

| | | |
|---|---|---|
| CN | 101217963 | 7/2008 |
| DE | 2508615 A | 9/1975 |

(56) References Cited

FOREIGN PATENT DOCUMENTS

| | | |
|---|---|---|
| DE | 10108614 A1 | 9/2002 |
| EP | 0036145 | 5/1985 |
| EP | 0184942 | 6/1986 |
| EP | 0537070 | 4/1993 |
| EP | 1103252 | 2/2000 |
| EP | 0981328 | 3/2000 |
| EP | 0988858 | 3/2000 |
| EP | 0724877 | 6/2000 |
| EP | 0904064 | 10/2001 |
| EP | 1624855 A2 | 2/2006 |
| EP | 1879456 A1 | 1/2008 |
| EP | 2000130 A1 | 12/2008 |
| EP | 2558073 | 2/2013 |
| FR | 2647346 | 11/1990 |
| FR | 2758459 | 11/1990 |
| GB | 1264677 | 2/1973 |
| GB | 2098865 | 12/1982 |
| GB | 2228198 A | 8/1990 |
| JP | S52-66616 | 6/1977 |
| JP | S52-148060 A | 12/1977 |
| JP | S57-70824 | 5/1982 |
| JP | 01139526 | 6/1989 |
| JP | H01-139526 | 6/1989 |
| JP | 07041422 | 2/1995 |
| JP | H07-508724 A | 9/1995 |
| JP | 09241152 | 9/1997 |
| JP | 11049664 | 2/1999 |
| JP | 11152227 | 6/1999 |
| JP | 2001-500368 | 1/2001 |
| JP | 2001-508445 | 6/2001 |
| JP | 2001-514626 | 9/2001 |
| JP | 2002-510311 | 4/2002 |
| JP | 2002-520377 | 7/2002 |
| JP | 2003-500368 | 1/2003 |
| JP | 2005500347 A | 1/2005 |
| JP | 2008537960 A | 10/2008 |
| JP | 2008-540451 | 11/2008 |
| JP | 5194209 | 5/2013 |
| WO | WO 82/01649 | 5/1982 |
| WO | WO 84/02076 | 6/1984 |
| WO | WO 88/00059 | 1/1988 |
| WO | WO 92/18147 | 10/1992 |
| WO | WO 1993/02664 | 2/1993 |
| WO | WO 93/06921 | 4/1993 |
| WO | WO 93/25192 | 12/1993 |
| WO | WO 94/25068 | 11/1994 |
| WO | WO 1995/01785 | 1/1995 |
| WO | WO 1995/01786 | 1/1995 |
| WO | WO 1995/24893 | 9/1995 |
| WO | WO 95/34287 | 12/1995 |
| WO | WO 96/17597 | 6/1996 |
| WO | WO 97/04749 | 2/1997 |
| WO | WO 1994/08610 | 4/1997 |
| WO | WO 97/40823 | 11/1997 |
| WO | WO 97/48382 | 12/1997 |
| WO | WO 1998/00116 | 1/1998 |
| WO | WO 98/30205 | 7/1998 |
| WO | WO 98/33512 | 8/1998 |
| WO | WO 1998/38984 | 9/1998 |
| WO | WO 1998/50077 | 11/1998 |
| WO | WO 1998/56357 | 12/1998 |
| WO | WO 99/00111 | 1/1999 |
| WO | WO 99/29300 | 6/1999 |
| WO | WO 99/40904 | 8/1999 |
| WO | WO 1999/44584 | 9/1999 |
| WO | WO 1999/48498 | 9/1999 |
| WO | WO 00/03753 | 1/2000 |
| WO | WO 00/16749 | 3/2000 |
| WO | WO 00/25772 | 5/2000 |
| WO | WO 00/37057 | 6/2000 |
| WO | WO 2000/50007 A1 | 8/2000 |
| WO | WO 00/57859 | 10/2000 |
| WO | WO 00/57918 | 10/2000 |
| WO | WO 2000/59482 A1 | 10/2000 |
| WO | WO 2000/59512 A1 | 10/2000 |
| WO | WO 00/71163 | 11/2000 |
| WO | WO 00/72825 | 12/2000 |
| WO | WO 00/76482 | 12/2000 |
| WO | WO 2001/01960 A1 | 1/2001 |
| WO | WO 2001/12155 A1 | 2/2001 |
| WO | WO 01/21154 | 3/2001 |
| WO | WO 2001/28555 A1 | 4/2001 |
| WO | WO 2001/37808 A1 | 5/2001 |
| WO | WO 01/49262 | 7/2001 |
| WO | WO 2002/39983 | 5/2002 |
| WO | WO 2003011300 A1 | 2/2003 |
| WO | WO 2003/068186 | 8/2003 |
| WO | WO 2004/087052 A2 | 10/2004 |
| WO | WO 2004/105694 A2 | 12/2004 |
| WO | WO 2005/041929 A2 | 5/2005 |
| WO | WO 2006/013369 A2 | 2/2006 |
| WO | WO 2006/113505 A2 | 10/2006 |
| WO | WO 2006-119498 A2 | 11/2006 |
| WO | WO 2007-018943 A2 | 2/2007 |
| WO | WO 2010/081032 | 7/2010 |
| WO | WO 2010/102737 | 9/2010 |
| WO | WO 2011/082384 A2 | 7/2011 |
| WO | WO 2011/129812 A1 | 10/2011 |
| WO | WO 2012/075081 A2 | 7/2012 |

OTHER PUBLICATIONS

U.S. Appl. No. 14/292,615, filed May 30, 2014; Satish Kumar Nachaegari; Office Action dated Oct. 26, 2015.
A.T. Burbello et al., Sovremennye lekarstvennyesredstava S—Pb "Neva," 2004, p. 567.
Addo, et al; "Non-polar extracts of serum from males contain covert radioimmunoassayable testosterone,"; Steroids, Sep. 1989, 54(3): 257-69.
Alvarez, F. J. and Stella, V. J., "The Role of Calcium Ions and Bile Salts on the Pancreatic Lipase-Catalyzed Hydrolysis of Triglyceride Emulsions Stabilized with Lecithin", Pharmaceutical Research, 6(6), 449-457 (1989).
Andriol® Testocaps™ Consumer Medicine Information, Sep. 2003.
Androderm® Product Label and Medication Guide; 1995; Labeler—Watson Pharma, Inc.; Revised Nov. 2013; 23 pages.
Androgel® Product Label and Medication Guide; May 2013; Labeler—AbbVie Inc.; Revised Oct. 2013; 28 pages.
Atkinson, et al.; Long Term experience with testosterone replacement through scrotal skin,: Testosterone: Action, Deficiency and Substitution (Nieschlag, E. and Behre, HM, eds.) 1998, Springer-Verlag, Berlin pp. 365-388.
Aungst (2000), "Intestinal Permeation Enhancers," Journal of Pharmaceutical Sciences 89(4):429-442.
Bagchus et al.; "Important Effect of Food on the Bioavailability of Oral Testosterone Undecanoate;" Pharmacotherapy (2003), vol. 23, No. 3; pp. 319-325.
Baluom et al. (1998), "The Importance of Intestinal Residence Time of Absorption Enhancer on Drug Implication on Formulative Considerations," International Journal of Pharmaceutics 176:21-30.
Bates, T. R. and Sequeira, J. A., "Bioavailability of Micronized Griseofulvin from Corn Oil-in-Water Emulsion, Aqueous Suspension, and Commercial Tablet Dosage Forms in Humans", Journal of Pharmaceutical Sciences, 64(5), 793-797(1975).
Beatch, G.N. et al., "Ventricular Fibrillation, an Uncontrolled Arrhythmia Seeking New Targets," Drug Dev. Res 55:45-52 (2002).
Bernkop-Schnurch (1998), "The Use of Inhibitory Agents to Overcome the Enzymatic Barrier to Perorally Administered Therapeutic Peptides and Proteins," Journal of Controlled Release 52:1-16.
Bhargava et al.; "Using microemulsions for drug delivery." Pharmaceutical Technology, Mar. 1987, pp. 46-53.
Cantrill, J.A.; "Which Testosterone Replacement Therapy?" Clinical Endocrinol (1984) 21:97-107.
Charman et al.; "Physicochemical and Physiological Mechanisms for the Effects of Food on Drug Absorption: The Role of Lipids and pH", Journal of Pharmceutical Sciences, 86(3), 269-282 (1997).
Constantindides, P., "Lipid Microemulsion for Improving Drug dissolution and Oral Absorption: Physical and Biopharmaceutical Aspect." Pharmaceutical Research, 1995; 12(11): 1561-1572.

(56) References Cited

OTHER PUBLICATIONS

Depo-Testosterone® Product Label and Medication Guide; Sep. 2006; Labeler—Pharmacia & Upjohn Company; Revised Aug. 2013; 12 pages.
Emulsion, IUPAC Compendium of Chemical Terminology, $2^{nd}$ Ed., 1997.
European Application No. 04 75 3162; Supplementary European Search Report dated Apr. 13, 2010.
European Application No. 06759173.5; Filed Jan. 23, 2008; David Fikstad; Supplementary European Search Report dated Mar. 11, 2010.
European Application No. 10 17 3114; European Search Report dated Apr. 14, 2011.
European Application No. 10729592.5; Supplementary Search Report dated Aug. 27, 2012.
Frey, H. et al., "Bioavailability of Oral testosterone in Males", Eur. J. Pharmacol. 16, 345-349 (1979).
Gennaro, A. R., Remington's Pharmaceutical Sciences, Chapter 20, 293-300 (1985).
Goncharova et al., "Preparation of Testosterone Esters," Pharmaceutical Chemical Journal 7(7):427-428 (1973).
Gooren; "A ten year safety study of the oral androgen testosterone undecanoate." J. Anch•ol., 1994, 15:212-215.
Graham-Smith et al., "The Oxford Reference-book in clinical Pharmacoloty and Pharmacotherapy," M. Meditsina Publishers, 2000, pp. 25, 136-137 (incl. Eng version).
Healthlink; [retrieved from on-line website (http://www.healthline.com/health/hypogonadism#Overview1), last visit on Apr. 14, 2015].
Hong, B.S., et al., Recent trends in the treatment of testosterone deficiency syndrome. International Journal of Urology, (2007) 14; 981-985.
Horter, D. and Dressman, J.B., "Influence of Physicochemical Properties on Dissolution of Drugs in the Gastrointestinal Tract", Advanced Drug Delivery Reviews 25, 3-14 (1997).
Houwing,N.S et al., "Pharmacokinetic Study in Women of Three Different Doses of a New Formulation of Oral Testosterone Undecanoate, Andriol Testocaps," Pharmacotherapy 23(10):1257-1265 (2003).
Humberstone, A. J. and Charman, W. N. "Lipid-based Vehicles for the Oral Delivery of Poorly Water Soluble Drugs", Advanced Drug Delivery Reviews, 103-128 (1997).
Hutchison,K. "Digestable Emulsions and Microenulsions for Optimum Oral Delivery of Hydrophobic Drugs," Bulletin Technique Gattefosse 87: 76-74 (1994).
Hydroxy Acid and Vitamin E; Stedman's Medical Dictionary ($22^{nd}$ Ed.); the Williams and Wilkins Company, 1973, p. 595 and 14000, Baltimore.
Javanbakht et al.; "Pharmacokinetics of a novel testosterone matrix transdermal system in health, premenopausal women and women infected with the human immunodeficiency virus"; Journal of Clinical Endocrinology & Metabolism 2000: 85(7): 2395-401.
Johnson, L. R., "Gastrointestinal Physiology", Department of Physiology, University of Texas Medical School, Houston,Texas, 25-26, 93, 106, 133-134, 136-137 (1997).
Julien, R.M., A Primer of Drug Action (Ninth Edition), 2001, p. 5-6.
Kalinchenko, S. Yu "Testosteron-korol' gormonov 1 gormon korolei", The Journal "Sex and Life", 2004, pp. 12-22 [online] retrieved on Mar. 26, 2010 13:27; Retrieved from the Internet:URL: http//www/laz.med.ru/interesting/publications/testosterone.html.
Langer, "New Methods of Drug Delivery," Science 249: 1527-1533 (1990).
Lecluyse et al. (1997), "In Vitro Models for Selection of Development Candidates. Permeability Studies to Define Mechanisms of Absorption Enhancement," Advanced Drug Delivery Reviews 23:163-183.
Leichtnam et al., "Testosterone Hormone Replacement Therapy: State-of-the-Art and Emerging Technology," Pharma. Res. 23(6): 1117-1132 (2006).
Lopezberestein and Fidler (eds.); Liposomes in the Therapy of Infectious Disease and Cancer; 1989; pp. 353-365; Liss; New York.

MacGregor, K. J. et al., "Influence of Lipolysis on Drug Absorption From the Gastro-intestinal Tract", Advanced Drug Delivery Reviews 25, 33-46 (1997).
Maisey et al.; Clinical Efficacy of Testosterone Undercanoate in Male Hypogonadism,; Clinical Endocrinology, 1981, vol. 14, pp. 625-629.
McAuley et al.; "Oral Administration of Micronized Progesterone: a Review and More Experience"; Pharmacotherapy, May 1996, 16(3): 453-457.
Meiner and Tonascia, "Clinical Trials: Design, conduct and Analysis," Monographs in Epidemiology and Biostatistics, 1986, vol. 8.
Merck Index ($11^{th}$ ed) "Vitamin E" and "Vitamin E Acetate", Monograph 9931 and 9932, Merck & Co., Inc., 1989, p. 1579-1580.
Merck Index ($12^{th}$ ed), "Fenofibrate" (Monograph 4019), Merck & Co., Inc. 1996. p. 675.
Merck Index, 12th Ed., "Shellac", Monograph 8623, Merck & Co. 1996, pp. 8526.
Merck Index, 12th Ed., "Testosterone", Monograph 9322, Merck & Co. 1996, pp. 1569.
Merriam-Webster Dictionary [online]; "Granule"; (Retrieved Dec. 17, 2009); Retrieved from the internet: URL: http://www.mw.com/dictionary/granule.
Mittal and Mukerjee, "The Wide World of Micelles"; International Business Machines Corporation and School of Pharmacy, University of Wisconsin, Madison 1976, vol. 1 Wisconsin; pp. 1-21.
Moellering RC. "Vancomycin: A 50-Year Reassessment". Clinical Infectious Diseases. 2006; 42:S3-S4.
Muranishi (1977), "Potential Absorption of Heparin from the Small Intestine and the Large Intestine in the Presence of Monoolein Mixed Micelles," Chem. Pharm. Bull. 24(5):1159-1161.
Muranishi (1990), "Absorption Enhancers," Critical Reviews in Therapeutic Drug Carrier Systems 7(1):1-33.
Nieschlag et al., "Plasma Androgen Levels in Men after Oral Administration of Testosterone or Testosterone Undecanoate," Acta Endocrinol. 79(2):366-374 (1975) (Abstract).
Noguchi T. et al., "The effect of drug lipophilicity and lipid vehicles on the lympathics absorption of various testosterone esters." International Journal of Pharmaceutics, 1985, 24:173-184.
Osol, ed.; Remington's Pharmaceutical Sciences ($15^{th}$ ed), 1975, Merck Publishing Co., pp. 327-339, 1452-1456.
PCT Application No. PCT/US04/16286; International Search Report dated May 8, 2006.
PCT Application No. PCT/US14/30604; Filing date Mar. 17, 2014; Lipocine Inc.; International Search Report dated Aug. 5, 2014.
PCT Application No. PCT/US2006/017445; Filed on May 4, 2006; Lipocine, Inc.; International Search Report dated Jul. 12, 2007.
PCT Application No. PCT/US2006/027159; Filed Jul. 12, 2006; Lipocine, Inc.; International Search Report dated Feb. 16, 2007.
PCT Application No. PCT/US2010/030788; Filed Apr. 12, 2010; Clarus Theraputics, Inc.; International Search Report dated Jan. 12, 2010.
PCT Application No. PCT/US2011/062538; Filed Nov. 30, 2011; Lipocine Inc. et al.; International Search Report dated Jun. 26, 2012.
PCT Application No. PCT/US2011/064495; Filed Dec. 12, 2011; Lipocine Inc. et al.; International Search Report dated Sep. 27, 2012.
PCT Application PCT/US2010/020538; Filed Jan. 8, 2010; Chandrashekar Giliyar; International Search Report dated Sep. 13, 2010.
Perchersky, A.V., et al. "Androgen administration in middle-aged and ageing men: effects of oral testosterone undecanoate on dihydrotestosterone, oestradiol and prostate volume." International Journal of Andrology, 25: 119-125 (2002).
Pouton, C. W., "Formulation of Self-Emulsifying Drug Delivery Systems", Advanced Drug Delivery Reviews 25, 47-58 (1997).
Reymond, J. and Sucker, H., "In Vitro Model for Ciclosporin Intestinal Absorption in Lipid Vehicles", Pharmaceutical Research, 5(10), 677-679.
S1 SEC filing (Securities and Exchange Commission) for Clarus Theraputics, Inc.; Filed May 23, 2014 with the Securities and Exchange Commission; 207 pages.

(56) References Cited

OTHER PUBLICATIONS

Saudek et al., A preliminary trial of the programmable implantable mediocatio system for insulin delivery, N.End.J.Med 321:574-579 (1989).
Schnabel et al., "The effect of food composition on serum testosterone levels after oral administration of ANdriol Testocaps," Clinical Endocrinology 66(4):570-585 (2007).
Schott, "Comments on Hydrophile-Lipophile Balance Systems," J.Pharm.Sci. 79(1):87-88 (1990).
Science lab.com; Material Safety Data Sheet Glyceryl monooleate MSDS; www.sciencelab.com; Oct. 2005; pp. 1-5.
Sefton, "Implantable pumps," CRC Crit. Rev. Biomed. Eng. 14(3):201-240 (1987).
Seidman, et al.; "Testosterone replacement therapy for hypogonadal men with SSRI-refractory depression"; Journal of Affective Disorders 48 (1998) 157-161.
Shackleford et al., Contribution of Lymphatically Transported Testosterone Undecanoate to the Systemic Exposure of Testosterone after Oral Administration of Two Andriol Formulations in Conscious Lymph Duct-Cannulated Dogs. The Journal of Pharmacology and Experimental Therapeutics. vol. 306, No. 3 (2003).
Shanghai Pi Chemicals Ltd. "Material Safety Data Sheet: Testosterone Undecanoate," Online 2007, retrieved Jun. 3, 2009 from http://www.pipharm.com/products/msds/msds-13457.pdf.
Stedman's Medical Dictionary ($22^{nd}$ Ed), "Dehydro-e-epiandrosterone", "Dehydroisoandrosterone" and "steroid", Williams and Wilkins, 1973, p. 329 and 1195-1197.
Stedman's Medical Dictionary ($22^{nd}$ Ed), "Surfactants" 1972, Williams and Wilkins Co., p. 1225.
Swerdoff, et al; "Long Term pharmaceokinetics of transdermal testosterone gel in hypogonadal men". J. Clin Endocrinol, Metab., 2000, 85:4500-4510.
Tarr, D. T. and Yalkowsky, S. H. "Enhanced Intestinal Absorption of Cyclosporine in Rats Through the Reduction of Emulsion Droplet Size", Pharmaceutical Research, 6(1), 40-43 (1989).
Tauber et al.; "Absolute bioavailability of testosterone after oral administration of testosterone-undecanoate and testosterone," Eur. J.Drug.Metabolism and Pharmacokinetics 11(2): 145-149 (1986).
Temina et al.; "Diversity of the fatty acids of the *Nostoc* species and their statistical analysis," Microbiological Research, 2007, pp. 308-321; Elsevier GmbH.
Tenover; "The Androgen-Deficient Aging Male: Current Treatment Options"; Reviews in Urology, 2003, vol. 5, Suppl. 1, S22-S28.
Testim® Product Label and Medication Guide; Sep. 2009; Labeler—A-S Medications Solutions LLC; Revised Jun. 2013; 17 pages.
The Merck Index, "Alpha Tocopherol"; Monograph 09571, Merck & Co., 2001-2004.
The Merck Index, "Carvedilol"; Monograph 01888, Merck & Co., 2001-2004.
The Merck Index, "Risperidone"; Monograph 08316, Merck & Co., 2001-2004.
The Merck Index, "Ziprasidone"; Monograph 10224, Merck & Co., 2001-2004.
The Merck Index, $12^{th}$ Ed., "Amiodarone", Monograph 504, Merck & Co., 1996, p. 84.
Torpac Inc.; Capsule Size Chart, Metric Table and English Table; www.torpac.com ; 2000 (retrieved from website Sep. 2014); 3 pages; Torpac Inc., Fairfield, New Jersey.
Treat, et al., "Liposomes in the Therapy of Infectious Diseases and Cancer", Lopez-Berestein and Fidler (eds.), Liss, New York, (1989), 353-365.
Tso, et al; "Intestinal Absorption and Lymphatic Transport of a High γ-Linolenic Acid Canola Oil in Lymph Fistula Sprague-Dawlwy Rats"; American society for Nutritional Sciences, 2002, pp. 218-221.
U.S. Appl. No. 10/444,935, filed May 22, 2003; Feng-Jing Chen; Office Action dated Dec. 1, 2011.
U.S. Appl. No. 10/444,935, filed May 22, 2003; Feng-Jing Chen; Office Action dated Apr. 20, 2009.
U.S. Appl. No. 10/444,935, filed May 22, 2003; Feng-Jing Chen; Office Action dated Apr. 29, 2011.
U.S. Appl. No. 10/444,935, filed May 22, 2003; Feng-Jing Chen; Office Action dated Aug. 4, 2010.
U.S. Appl. No. 10/444,935, filed May 22, 2003; Feng-Jing Chen; Office Action dated Feb. 8, 2008.
U.S. Appl. No. 10/444,935, filed May 22, 2003; Feng-Jing Chen; Office Action dated Jan. 11, 2010.
U.S. Appl. No. 10/444,935, filed May 22, 2003; Feng-Jing Chen; Office Action dated Jul. 6, 2005.
U.S. Appl. No. 10/444,935, filed May 22, 2003; Feng-Jing Chen; Office Action dated Mar. 7, 2006.
U.S. Appl. No. 10/444,935, filed May 22, 2003; Feng-Jing Chen; Office Action dated Nov. 2, 2006.
U.S. Appl. No. 10/444,935, filed May 22, 2003; Feng-Jing Chen; Office Action dated Oct. 28, 2008.
U.S. Appl. No. 10/444,935, filed May 22, 2003; Feng-Jing Chen; Office Action dated Sep. 23, 2013.
U.S. Appl. No. 10/764,016, filed Jan. 23, 2004; David Fikstad; Office Action dated Apr. 20, 2006.
U.S. Appl. No. 10/764,016, filed Jan. 23, 2004; David Fikstad; Office Action dated Feb. 23, 2009.
U.S. Appl. No. 10/764,016, filed Jan. 23, 2004; David Fikstad; Office Action dated Apr. 24, 2008.
U.S. Appl. No. 10/764,016, filed Jan. 23, 2004; David Fikstad; Office Action dated Jul. 13, 2005.
U.S. Appl. No. 10/764,016, filed Jan. 23, 2004; David Fikstad; Office Action dated Jul. 24, 2008.
U.S. Appl. No. 10/764,016, filed Jan. 23, 2004; David Fikstad; Office Action dated Sep. 7, 2007.
U.S. Appl. No. 10/764,016, filed Jan. 23, 2004; David Fikstad; Office Action dated Dec. 19, 2006.
U.S. Appl. No. 11/122,788, filed May 4, 2005; David Fikstad; Office Action dated Jun. 9, 2009.
U.S. Appl. No. 11/122,788, filed May 4, 2005; David Fikstad; Office Action dated May 6, 2014.
U.S. Appl. No. 11/122,788, filed May 4, 2005; David Fikstad; Office Action dated Dec. 9, 2009.
U.S. Appl. No. 11/122,788, filed May 4, 2005; David Fikstad; Office Action dated Feb. 11, 2015.
U.S. Appl. No. 11/196,805, filed Aug. 2, 2005; Mahesh Patel; Office Action dated Sep. 2, 2008.
U.S. Appl. No. 12/326,711, filed Dec. 2, 2008; Mahesh Patel; Office Action dated Jul. 19, 2013.
U.S. Appl. No. 12/326,711, filed Dec. 2, 2008; Mahesh Patel; Office Action dated Feb. 14, 2014.
U.S. Appl. No. 12/326,711, filed Dec. 2, 2008; Mahesh Patel; Office Action dated Nov. 9, 2010.
U.S. Appl. No. 12/326,711, filed Dec. 2, 2008; Mahesh Patel; Office Action dated Sep. 16, 2011.
U.S. Appl. No. 12/326,711, filed Dec. 2, 2008; Mahesh Patel; Office Action dated Mar. 30, 2011.
U.S. Appl. No. 12/326,711, filed Dec. 2, 2008; Mahesh Patel; Office Action dated Sep. 29, 2009.
U.S. Appl. No. 12/350,930, filed Jan. 8, 2009; Chandraschekar Giliyar; Office Action dated Apr. 2014.
U.S. Appl. No. 12/350,930, filed Jan. 8, 2009; Chandraschekar Giliyar; Office Action dated Nov. 29, 2010.
U.S. Appl. No. 12/350,930, filed Jan. 8, 2009; Chandraschekar Giliyar; Office Action dated Mar. 28, 2011.
U.S. Appl. No. 12/625,284, filed Nov. 24, 2009; Feng-Jing Chen; Office Action dated Jan. 4, 2012.
U.S. Appl. No. 12/625,284, filed Nov. 24, 2009; Feng-Jing Chen; Office Action dated Jul. 24, 2012.
U.S. Appl. No. 12/625,284, filed Nov. 24, 2009; Feng-Jing Chen; Office Action dated Mar. 10, 2014.
U.S. Appl. No. 12/625,284, filed Nov. 24, 2009; Feng-Jing Chen; Office Action dated Dec. 8, 2014.
U.S. Appl. No. 12/625,309, filed Nov. 24, 2009; Feng-Jing Chen; Office Action dated Jan. 27, 2012.
U.S. Appl. No. 12/625,309, filed Nov. 24, 2009; Feng-Jing Chen; Office Action dated Feb. 13, 2013.

(56) References Cited

OTHER PUBLICATIONS

U.S. Appl. No. 12/625,309, dated Nov. 24, 2009; Feng-Jing Chen; Office Action dated Aug. 6, 2012.
U.S. Appl. No. 12/957,206; Filed Nov. 30, 2010; Chandrashekar Giliyar; Office Action dated Mar. 1, 2013.
U.S. Appl. No. 12/957,206, filed Nov. 30, 2010; Chandrashekar Giliyar; Office Action dated Jul. 18, 2013.
U.S. Appl. No. 12/957,206, filed Nov. 30, 2010; Chandrashekar Giliyar; Office Action dated Sep. 15, 2014.
U.S. Appl. No. 12/965,703, filed Dec. 10, 2010; Basawaraj Chickmath; Office Action dated Jun. 15, 2012.
U.S. Appl. No. 12/965,703, filed Dec. 10, 2010; Basawaraj Chickmath; Office Action dated Oct. 23, 2012.
U.S. Appl. No. 12/965,703, filed Dec. 10, 2010; Basawaraj Chickmath; Office Action dated Feb. 27, 2014.
U.S. Appl. No. 12/965,703, filed Dec. 10, 2010; Basawaraj Chickmath; Office Action dated Jul. 1, 2014.
U.S. Appl. No. 12/965,703, filed Dec. 10, 2010; Basawaraj Chickmath; Office Action dated May 5, 2015.
U.S. Appl. No. 13/029,989, filed Feb. 17, 2011; Feng-Jing Chen; Office Action dated Dec. 4, 2012.
U.S. Appl. No. 13/029,989, filed Feb. 17, 2011; Feng-Jing Chen; Office Action dated Mar. 19, 2013.
U.S. Appl. No. 13/029,989, filed Feb. 17, 2011; Feng-Jing Chen; Office Action dated Nov. 18, 2013.
U.S. Appl. No. 13/485,807, filed May 31, 2012; Chandrashekar Giliyar; Office Action dated Nov. 14, 2013.
U.S. Appl. No. 13/485,807, filed May 31, 2012; filed May 31, 2012; Chandrashekar Giliyar; Office Action dated Nov. 14, 2013.
U.S. Appl. No. 13/485,807, filed May 31, 2012; Chandrashekar Giliyar; Office Action dated Sep. 25, 2014.
U.S. Appl. No. 13/485,807, filed May 31, 2012; Chandrashekar Giliyar; Office Action dated Apr. 30, 2014.
U.S. Appl. No. 13/592,258, filed Aug. 22, 2012; Chandraschekar Giliyar; Office Action dated Jan. 26, 2013.
U.S. Appl. No. 13/592,258, filed Aug. 22, 2012; Chandraschekar Giliyar; Office Action dated Mar. 19, 2013.
U.S. Appl. No. 13/592,258, filed Aug. 22, 2012; Chandraschekar Giliyar; Office Action dated Oct. 26, 2012.
U.S. Appl. No. 13/592,258, filed Aug. 22, 2012; Chandrashekar Giliyar; Office Action dated Aug. 6, 2013.
U.S. Appl. No. 13/592,258, filed Aug. 22, 2012; Chandrashekar Giliyar; Office Action dated Mar. 4, 2014.
U.S. Appl. No. 13/663,352, filed Oct. 29, 2012; David Fikstad; Office Action dated Jan. 10, 2014.
U.S. Appl. No. 13/663,352, filed Oct. 29, 2012; David Fikstad; Office Action dated Jul. 23, 2014.
U.S. Appl. No. 13/843,403, filed Mar. 15, 2013; Satish Kumar Nachargari; Office Action dated Mar. 17, 2014.
U.S. Appl. No. 13/843,403, filed Mar. 15, 2013; Satish Kumar Nachargari; Office Action dated May 27, 2014.
U.S. Appl. No. 13/843,403, filed Mar. 15, 2013; Satish Kumar Nachegari; Office Action dated Apr. 15, 2015.
U.S. Appl. No. 14/191,249, filed Feb. 26, 2014; Chandrashekar Giliyar; Office Action dated Nov. 20, 2014.
U.S. Appl. No. 14/191,249, filed Feb. 26, 2014; Chandrashekar Giliyar; Office Action dated Jul. 8, 2014.
U.S. Appl. No. 14/191,278, filed Feb. 26, 2014; Chandrashekar Giliyar; Office Action dated Jul. 8, 2014.
U.S. Appl. No. 14/319,051, filed Jun. 30, 2014; Satish Kumar Nachaegari; Office Action dated Jun. 5, 2015.
U.S. Appl. No. 14/319,077, filed Jun. 30, 2014; Satish Kumar Nachaegari; Office Action dated Jul. 20, 2015.
U.S. Appl. No. 12/957,206, filed Nov. 30, 2010; Chandrashekar Giliyar; Office Action dated Jul. 27, 2015.
U.S. Appl. No. 14/801,674, filed Jul. 16, 2015; Chandrashekar Giliyar; Office Action dated Sep. 2, 2015.
U.S. Appl. No. 14/633,545, dated Feb. 27, 2015; Chandrashekar Giliyar; Office Action dated Aug. 20, 2015.
U.S. Appl. No. 14/801,737, dated Jul. 16, 2015; Chandrashekar Giliyar; Office Action dated Aug. 19, 2015.
U.S. Appl. No. 14/535,536, filed Nov. 7, 2014; Feng-Jing Chen; Office Action dated Feb. 5, 2015.
Wang, et al; "Long-term testosterone gel (AndroGel®) treatment maintains beneficial effects on sexual function and mood, lean and fat mass and bone mineral density in hypogonadal men"; J. Clin. Metab., 2004, 89-2085-2098.
Wilson, C.G. and O'Mahony, B., "The Behaviour of Fats and Oils in the Upper G.I. Tract," Bulletin Technique Gattefosse 90: 13-18 (1997).
Winne, D., "Dependence of Intestinal Absorption in Vivo on the Unstirred Layer", Archives of Pharmacology, 304, 175-181 (1978).
Yassin et al.; "Long-acting testosterone undecanoate for parenteral testosterone therapy"; Therapy, Future Drugs, 2006, 3(6): 709-721.
Yin et al., "Dietary Fat Modules Testosterone Pharmacokinetics of a New Self-Emulsifying Formulation of Oral Testosterone Undercanoate in Hypogonadal Men." Submitted Journal of Andrology, submitted Mar. 23, 2012, published ahead of print on Jul. 12, 2012.
Yin et al.; "Reexamination of Pharmacokinetics of Oral Testosterone Undercanoate in Hypogonadal Men with a New Self-Emulsifying Formulation"; Journal of Andrology 2012, 33(2): 190-201.
Zhi et al., "effects of dietary fat on drug absorption," Clin. Pharmacol. & Ther. 58:487-491 (1995).
Notice of allowance for U.S. Appl. No. 14/298,768 dated Feb. 8, 2016, 37 pages.
Office action for U.S. Appl. No. 14/500,438 dated Feb. 1, 2016, 50 pages.
Office action for U.S. Appl. No. 14/952,796 dated Mar. 15, 2016, 11 pages.

\* cited by examiner

TESTOSTERONE UNDECANOATE COMPOSITIONS

CROSS-REFERENCE TO RELATED APPLICATIONS

This application is a divisional application of U.S. patent application Ser. No. 12/965,703 filed Dec. 10, 2010, which is incorporated herein by reference in its entirety.

FIELD OF THE INVENTION

The present invention relates to solid testosterone undecanoate containing pharmaceutical compositions and oral dosage forms as well as associated methods of treatment. Accordingly, this invention involves the fields of chemistry, pharmaceutical sciences, medicine and other health sciences.

BACKGROUND OF THE INVENTION

The need for testosterone supplementation, often caused by testosterone deficiency, is a condition that can affect both men and women. Testosterone deficiency can be accompanied by a variety of symptoms including sexual dysfunction, reduced muscle mass and muscle strength, depressed mood, and osteoporosis. Male hypogonadism and female sexual dysfunction is characterized by a deficiency of endogenous testosterone production resulting in abnormally low levels of circulating testosterone. Currently, common testosterone therapy treatment can include administration of invasive intramuscular products, topical gels, topical solution and patches, or multiple units of liquid oral dosage capsules. There are challenges and drawbacks associated with each of these therapies. For example, use of topical gels or topical solutions can result in accidental transfer of the active agent to others, such as children or partners.

Current standard therapies for males aim at restoring physiologically relevant levels of testosterone in serum. It is generally recognized that in a normal adult man of age 17 to 54 yrs, the average serum testosterone (T) a major androgenic hormone in males, is between about 300 ng/dL to about 1100 ng/dL, known as the eugonadal range. Testosterone replacement in males should in theory approximate the natural, endogenous production of the hormone. The average male produces 4-7 mg of testosterone per day in a circadian pattern, with maximal plasma levels attained in early morning and minimal levels in the evening.

Low or reduced sexual desire is a condition that impacts millions of women, particularly those over the age of 50. Testosterone (T) levels can steeply decline in women as they age or after surgical menopause. Endogenous testosterone levels in women at age 40 are one half of those of women at age 21 and endogenous testosterone levels in women after oophorectomy are 50% less than before oophorectomy. There is strong indication that supplemental testosterone therapy may be beneficial for the treatment of women with reduced sexual desire. Currently in the United States, there is no approved testosterone product available for the treatment of female sexual dysfunction and reduced sexual desire. The human female has substantially lower normal blood levels of total testosterone (10-100 ng/dL compared to males ~300-1100 ng/dL) so it can be logically surmised that efficacious doses for women can be substantially lower (about 10-50 times) than that for men.

While oral is typically the most preferred and patient friendly route for administration, the oral delivery of testosterone as testosterone remains a huge challenge. This is due to extremely poor bioavailability requiring very high dose as well as the short serum half-life requiring frequent dosing. These problems with orally administered testosterone are primarily due to first pass metabolism. Moreover, direct, oral delivery of testosterone is also known to cause enzyme induction resulting in potential drug-drug interactions. Currently, modified testosterones, in form of methyl analogue of testosterone, and as an undecanoate ester, testosterone undecanoate (TU) are available for oral administration for patients in need of testosterone therapy. However, liver damage including cholestasis, peliosis hepatitis, nodular regenerative hyperplasia, and primary hepatic tumors has been reported with use of methyl testosterone. Testosterone undecanoate, a prodrug of testosterone, containing oral dosage forms are marketed in various countries under various trade names, e.g. Andriol®, Restandol®, Andriol Testocap® etc., each of which are liquid filled soft-gelatin capsule formulations containing about 40 mg of TU in a liquid carrier. Testosterone undecanoate is converted in vivo to pharmacologically active testosterone.

However, a huge drawback of the current state of the art oral liquid testosterone undecanoate formulations is that it has to be encapsulated in a capsule dosage form presenting it with limitations with respect to acceptable capsule sizes and related drug loading limitations due to testosterone undecanoate's poor solubility. Such limitations present challenges with respect to patient compliance, because patients typically have to take multiple capsule units in order to get a sufficient dose to provide the desired efficacy. Additionally, liquid capsule formulations tend to require more complicated and costly manufacturing processes and often require special storage and handling. Moreover, liquid lipidic compositions can present oxidative instability challenges with respect to testosterone and its derivatives. Due to testosterone undecanoate's poor solubility, the production of a solid oral dosage forms such as tablets, caplets, and particulates remains an area of continuous research and development.

SUMMARY OF THE INVENTION

The present disclosure is drawn to pharmaceutical compositions and oral dosage forms containing testosterone undecanoate, as well as related methods of treatment. In one embodiment, a solid composition is provided. The dosage form can include a therapeutically effective amount of testosterone undecanoate and a pharmaceutically acceptable carrier. The oral dosage form can be formulated to release at least 35 wt % of the dosage form's testosterone undecanoate in the first 120 minutes when measured using a USP Type II apparatus in 1000 mL of 8 wt % Triton X-100 in water at 37° C. and 100 rpm. In one embodiment, the testosterone undecanoate can be present in the composition as a solid particulate. In yet a further embodiment, the carrier can be free of lipid substance, or lipophilic surfactant or hydrophilic surfactants.

In another embodiment, a solid oral dosage form is provided. The oral dosage form can include a therapeutically effective amount of testosterone undecanoate and a pharmaceutically acceptable carrier. The dosage form can be formulated such that, when measured using a USP Type II apparatus in 1000 mL of 8 wt % Triton X-100 in water at 37° C. and 100 rpm, the oral dosage form releases at least 20% more testosterone undecanoate after the first 120 minutes than an equivalent dose testosterone undecanoate containing oral dosage form without the pharmaceutically acceptable carrier. In one embodiment, testosterone undecanoate is not present in the solid composition in a solubilized form. In another embodiment the oral dosage form can be formulated to include the testosterone undecanoate dose in the form of solid particulates. In another embodiment the oral dosage form of this invention can include a composition comprising solid particulates that can be solid testosterone undecanoate and/or a solid pharmaceutically acceptable carrier.

In yet another embodiment, a method for treating a subject in need of testosterone therapy is provided. The method includes administering a solid oral dosage form of the present invention. In one embodiment, the administration can be once daily. In another embodiment, the administration can be once every twelve hours.

DETAILED DESCRIPTION

Before the present testosterone undecanoate compositions, oral dosage forms and related methods of use are disclosed and described, it is to be understood that this invention is not limited to the particular process steps and materials disclosed herein, but is extended to equivalents thereof, as would be recognized by those ordinarily skilled in the relevant arts. It should also be understood that terminology employed herein is used for the purpose of describing particular embodiments only and is not intended to be limiting.

It should be noted that, the singular forms "a," "an," and, "the" include plural referents unless the context clearly dictates otherwise. Thus, for example, reference to "an excipient" includes reference to one or more of such excipients, and reference to "the carrier" includes reference to one or more of such carriers.

Definitions

As used herein, the term "treatment," when used in conjunction with the administration of pharmaceutical compositions and oral dosage form containing testosterone undecanoate, refers to the administration of the oral dosage form and pharmaceutically acceptable composition to subjects who are either asymptomatic or symptomatic. In other words, "treatment" can both be to reduce or eliminate symptoms associated with a condition or it can be prophylactic treatment, i.e. to prevent the occurrence of the symptoms. Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Furthermore, the term "dosage form" can include one or more formulation(s) or composition(s) provided in a format for administration to a subject. When any of the above terms is modified by the term "oral" such terms refer to compositions, formulations, or dosage forms formulated and intended for oral administration to subjects.

As used herein, the term "lipophilic" when used in combination with both solid and liquid lipophilic additives, refers to additives that have poor or no solubility in water. "Lipophilic surfactants" refer to lipophilic additives that have HLB values of 10 or less, preferably between 2 to 10. Conversely, the term "hydrophilic," when used in combination with both solid and liquid hydrophilic additives, refers to additives that have average or good solubility in water.

"Hydrophilic surfactants" are hydrophilic additives that have significant surface active property and that have HLB values of more than 10.

As used herein, the term "lipid" or lipid substance" as used in connection, with various compounds, refers to fatty acid (unless otherwise specified, having chain length greater than $C_6$) or fatty acid esters or glycerides of fatty acid esters, mixtures thereof and derivatives thereof, although not including salts thereof.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals. In one embodiment, the subject is a human subject. In one embodiment, the human subject is a male. In another embodiment, the human subject is a female.

As used herein, the term "solid particulate" means relating to, or formed of minute separate particles, as of a granular substance or powder and that is a solid at room temperature. The term "multiparticulate" represents coated or uncoated drug delivery system, in which the dosage of the drug is divided among several discrete delivery entities, in contrast to a single-unit delivery entity. Multiparticulate systems can be powder, granule, mini-tablets, beads, prills, pellets, or combinations thereof. The term "matrix" represents coated or uncoated drug delivery system, in which the dosage of the drug is a single-unit monolithic delivery entity, such as tablet.

The term "oral administration" represents any method of administration in which an active agent can be administered by swallowing, chewing, or sucking of the dosage form; or admixing the dosage form or its contents with food and/or beverage immediately prior to consuming.

As used herein, the terms "release", "release rate", are used interchangeably to refer to the discharge or liberation of a substance, including without limitation a drug, from the dosage form into a surrounding environment such as an aqueous medium either in vitro or in vivo.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics, Vol.* 8 (1986), incorporated herein by reference.

As used herein, the term "$C_{avg}$" or "C-average" is used interchangeably, and is determined as the $AUC_{0-t}$ or the mean AUC divided by the time period (t). For example, $C_{avg-8\,h}$ is the average plasma concentration over a period of 8 hours post-dosing determined by dividing the $AUC_{0-8}$ value by 8. Similarly, $C_{avg-12\,h}$ is the average plasma concentration over a period of 12 hours post-dosing determined by dividing the $AUC_{0-12}$ value by 12; $C_{avg-24\,h}$ is the average plasma concentration over a period of 24 hours post-dosing determined by dividing the $AUC_{0\text{-}24\,h}$ value by 24, and so on.

For the purpose of this invention, the average baseline plasma testosterone concentration (T-$C_{avg\text{-}B}$) of the human subject refers to the arithmetic mean of the total plasma testosterone concentrations determined on at least two consecutive times prior to any androgen treatment. In one aspect, the plasma testosterone concentration of the human male can be determined by automated or manual immunoassay methods, liquid chromatography or liquid chromatography-tandem mass spectrometry (LC-MSMS) methods or equivalent methods or combination of methods thereof.

As used herein, the terms "plasma testosterone concentration", "serum testosterone concentration" or "testosterone concentration in blood" are used interchangeably and refers to the total testosterone including both free and bound testosterone, present in the plasma, serum or blood of a subject.

The terms "carrier" or "pharmaceutically acceptable carrier" are used interchangeably and refer to a pharmaceutically acceptable substances that enable a solid dosage form and that alter the release rate and/or extent of the active agent, for example testosterone undecanoate, from the composition and/or the dosage form. In one aspect of the invention, a pharmaceutically acceptable carrier is a compound or a mixture of compounds that enables the release of testosterone undecanoate from an oral dosage composition, when tested using a USP Type II apparatus in 1000 mL of 8 wt % Triton X-100 in water at 37° C. and 100 rpm, such that the oral dosage form releases at least 20% more testosterone undecanoate after the first 120 minutes compared to an equivalent dose testosterone undecanoate oral dosage form without the pharmaceutically acceptable carrier.

As used herein, the term "delayed release" is defined as release of testosterone undecanoate from the composition or oral dosage form which, upon contact with an aqueous medium, occurs in a time delayed manner attributed either to the characteristics of the dosage form via for example, coating, encapsulating shell, etc., or due to the inherent nature of the composition. When the oral dosage form or composition includes a conventional capsule shell, the delay in release is calculated after the capsule shell is dissolved or compromised.

As used herein, the term "about" is used to provide flexibility to a numerical range endpoint by providing that a given value may be "a little above" or "a little below" the endpoint. As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, a pharmaceutical "formulation" or "composition" is defined as including a pharmaceutically active agent and a pharmaceutically acceptable carrier that may or may not be processed or incorporated into a dosage form.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Invention

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, variants, modifications, and equivalents as may be included within the spirit and scope of the invention as defined by the appended claims.

The present disclosure is drawn to pharmaceutical compositions and oral dosage forms containing testosterone undecanoate, as well as related methods of treatment. In particular, it has been discovered that testosterone undecanoate can be formulated into solid compositions containing solid testosterone undecanoate that are capable of providing the necessary release, in vitro or in vivo, and bioavailability to provide therapeutic effectiveness. For example, in one embodiment, a solid oral dosage form is provided. The solid oral dosage form can include a therapeutically effective amount of testosterone undecanoate and a pharmaceutically acceptable carrier. The solid oral dosage form can include a solid composition comprising a therapeutically effective amount of testosterone undecanoate and a pharmaceutically acceptable carrier. The solid composition of the present invention can be formulated to release at least 35 wt % of its testosterone undecanoate in the first 120 minutes, when measured using a USP Type II apparatus in 1000 mL of 8 wt % Triton X-100 in water at 37° C. and 100 rpm. Similarly, the oral dosage form can be formulated to release at least 35 wt % of the dosage form's testosterone undecanoate in the first 120 minutes when measured using a USP Type II apparatus in 1000 mL of 8 wt % Triton X-100 in water at 37° C. and 100 rpm.

In another embodiment, a solid oral dosage form is provided. The oral dosage form can include a therapeutically effective amount of testosterone undecanoate and a pharmaceutically acceptable carrier. The dosage form can be formulated such that, when measured using a USP Type II apparatus in 1000 mL of 8 wt % Triton X-100 in water at 37° C. and 100 rpm, the oral dosage form releases at least 20% more testosterone undecanoate after the first 120 minutes than a equivalent dose testosterone undecanoate containing oral dosage form without the pharmaceutically acceptable carrier. The oral dosage forms and related solid compositions disclosed herein do not form oil-in-water emulsions when contacted with water with adequate mixing within 15 minutes as observed by appearance of uniform opaque or translucent liquid or by other appropriate means. The term "oil in water (O/W) emulsion," as used herein, refers to a multi-phase system wherein oil or oil-like small globules are dispersed in water. Such globules can have the average diameters of greater than about 200 nm or exhibit absorbance of about 0.5 or more when spectrophotometrically measured at about 400 nm. The oil or oil-like globules can have the tendency to coalesce and are distinctly different from thermodynamically stable micelles or microemulsions.

The oral dosage forms and related solid compositions disclosed herein do not include lipid substance. The oral dosage forms and related solid compositions disclosed herein do not include lipid substance having a fatty acid chain length greater than $C_{12}$.

In one embodiment, the oral dosage form of this invention can include a solid particulate which can be solid testosterone undecanoate and/or a solid pharmaceutically acceptable carrier. The solid oral dosage form of the present invention can be administered as any oral dosage form known in the art. Specific examples of oral dosage forms include tablets, capsules, sachets, lozenges, granules, powders, fast melt, lyophilized, sprinkle, suspension or combinations thereof. In another embodiment, the dosage form is coated. In one embodiment, the solid composition can be a matrix. In one embodiment, the solid oral dosage form is a tablet or a capsule. In another embodiment oral dosage form is a multiparticulate oral dosage form. In another embodiment, the composition can be multiparticulate. Regardless of the type, the oral dosage forms or compositions can be formulated to provide modified, delayed, sustained, extended, and/or controlled release of the testosterone undecanoate. The modified, delayed, extended, pulsatile, and/or controlled release can be achieved by any method known in the art so long as it does not interfere with the function of the solid oral dosage forms. Non-limiting examples of such methods includes coatings, polymers, and the like. In one embodiment, the oral dosage form can be uncoated. In one embodiment the solid composition of the invention is a solid dispersion, solid solution, molecular dispersion, co-precipitate, amorphate, solidified suspension, admixture, eutectic mixture, melt extrude, drug-carrier complex, thermosetting system, or combinations thereof.

The compositions of this invention can include compounds or systems that increase mean residence time of the composition/dosage form in the gastrointestinal tract to enable prolonged drug release resulting in longer duration of action. This can be accomplished by using approaches that delays stomach emptying, mucoadhesion, floatation, sedimentation, expansion, and/or modified shape systems.

The solid oral dosage forms the present invention can be manufactured as tablet or capsule dosage forms either by dry granulation methods, or by wet granulation methods. For example, testosterone undecanoate can be combined with one or more pharmaceutically acceptable carrier and blended to get a homogenous mixture which can be compressed into a tablet or disposed into a capsule. In another embodiment, the homogenous mixture can be kneaded with a binder solution to get a wet granulate mass which can be dried and sized, for example by passing through ASTM mesh #30. The resulting granules can be optionally blended with pharmaceutical aids such as diluents, lubricants, disintegrants etc, and disposed into capsules or compressed into tablets. In another particular case, the tablets can be coated.

In one embodiment the tablet is a matrix tablet. In another embodiment, the tablet can be multi-layered tablet dosage form which can achieve release characteristics that can accommodate dose splitting.

The solid oral dosage forms can also be formulated using melt-extrusion processes alone or in combination with other known processes. For example, in one embodiment, an amount of testosterone undecanoate can be homogeneously combined with a sufficient amount of one or more carrier substances prior to undergoing extrusion. The carrier suitable for the compositions of this invention, specifically melt extrusion process, can be lipophilic or hydrophilic carrier. Combinations of lipophilic and hydrophilic carriers may also be used.

For the purpose of current invention, the terms "melt" and "melting" should be interpreted broadly, and include not only the alteration from a solid state to a liquid state, but can also refer to a transition to a glassy state or a rubbery state in which it is possible for one component of the mixture to get embedded more or less homogeneously into the other. In particular cases, one component can melt and the other component(s) can dissolve in the melt, thus forming a solution which, upon cooling, may form a solid composition having advantageous properties. In another particular case, one component can melt and the other component(s) can suspend thus forming a suspension which upon cooling may form a solid suspension having advantageous properties.

The melt-extruded solid compositions used to make the solid oral dosage forms of the present disclosure can be granular, multiparticulates, pellets, beads, mini-tablets or tablets. The melt-extruded solids can be used alone as the solid oral dosage form or can be disposed into capsules or formed into tablets.

The carrier for a melt-extruded composition and/or dosage form can include, but is not limited to, carriers such as ethyl cellulose, cellulose acetate phthalates, glyceryl distearate, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly (methacrylic acid) (anhydride), methyl methacrylate, polymethacrylate, stearic acid, poly(methyl methacrylate) copolymer, polyacrylamide, aminoalkyl methacrylate copolymer, poly(methacrylic acid anhydride), and glycidyl methacrylate copolymers.

In one embodiment, the carrier for a melt-extruded solid oral dosage form can be one or more pharmaceutically acceptable polymers including, but not limited to polyvinyl alcohol, polyvinyl pyrrolidone, polyethylene glycols having molecular weight of about 1000 to about 20,000, gelatin, carbomer, poloxamer, hydroxypropyl methyl cellulose; hydroxypropyl ethyl cellulose hydroxypropyl cellulose, carboxymethyl cellulose. It is noteworthy that some pharmaceutical carriers can be used in more than one manufacturing process, such as a wet milling or dry milling process as well as a melt extrusion process.

In a further aspect, the compositions of the current invention can be formulated to provide a gastro-retentive dosage form. In one embodiment, the gastro-retentive dosage form can be a capsule or a tablet. In another embodiment, the gastro-retentive dosage form can be retained in the upper gastro intestinal tract for at least one hour post-dosing. In another embodiment, the gastro-retentive dosage form can be retained in the upper gastro intestinal tract for at least two hours post-dosing. In another embodiment, the gastro-retentive dosage form can be retained in the upper gastro intestinal tract for at least 4 hours post-dosing. In another embodiment, the gastro-retentive dosage form can be formulated to float in the upper gastro intestinal tract after dosing. In another embodiment, the gastro-retentive dosage form is formulated to increase in the dosage form volume by at least 10% when it comes in contact with an aqueous use environment compared to its volume when it is not in contact with the aqueous use environment. In another embodiment, the gastro-retentive dosage form is formulated to adhere to the lining of the upper gastro intestinal tract wall after dosing.

The compositions and the oral dosage forms of the current invention can also include one or more of the pharmaceutical process aids selected from the group known in the art, consisting of binders, bufferants, diluents, disintegrants, flavors, colorants, taste-masking agents, resins, pH modifiers, lubricants, glidants, thickening agent, opacifying agent, humectants, desiccants, effervescing agents, plasticizing agents and the like.

In a further aspect, the dosage form can comprise two or more of populations of testosterone undecanoate compositions of the present invention. In one embodiment, at least one of the populations can be formulated to start releasing testosterone undecanoate immediately into a surrounding aqueous medium. In another embodiment, at least one of the populations can be formulated to start releasing testosterone undecanoate after at least 2 hours. In another embodiment, at least one the populations can be formulated to release testosterone undecanoate after about 4 hours, or after about 6 hours, or after about 8 hours, or after about 10 hours, into a surrounding aqueous medium.

In yet a further embodiment, at least one of the populations can be formulated to start releasing testosterone undecanoate immediately after oral administration to a human. In one particular case, at least one of the populations can be formulated to start releasing testosterone undecanoate in the duodenal region after oral administration to a human. In another particular case, at least one of the populations can be formulated to start releasing testosterone undecanoate in the small intestine after oral administration to a human.

In yet a further embodiment, at least one of the populations includes a pH sensitive substance. In a particular case, at least one of the populations can be formulated to start releasing testosterone undecanoate at a pH of from about 1.0 to about 3.4. In another particular case, at least one of the populations can be formulated to start releasing testosterone undecanoate at a pH of from about 3.5 to about 5.5. In another particular case, at least one of the populations can be formulated to start releasing testosterone undecanoate at a pH of from about 5.6 to about 6.8. In another particular case, at least one of the populations can be formulated to start releasing testosterone undecanoate at a pH about 7.0 or more.

In yet another aspect, the dosage form comprising two or more of populations of testosterone undecanoate compositions of the present invention is a capsule or a tablet or a granular admixture. In a particular case, the dosage form is a capsule-in-capsule dosage form. In another particular case the dosage form is a tablet-in-capsule dosage form. In another particular case the dosage form is a tablet-in-tablet dosage form. In another particular case, the dosage form is a granules and/or pellets in capsule dosage form. In another particular case, the dosage form is a granule, pellet and/or tablet in a capsule dosage form.

Non-limiting examples of the processes that can be used to prepare the compositions and dosage forms of this invention include mixing melting, prilling, size reduction, melt-spray congealing, co-precipitation, co-crystallization, encapsulation, co-milling, spray or freeze drying, complexing, granulating, extruding, slugging, or combinations thereof.

The amount of testosterone undecanoate present in the oral dosage forms of the present invention can vary depending on the desired therapeutic effect. For example, a solid oral dosage form intended to provide treatment of hypogonadism in males would likely have a greater amount of testosterone undecanoate present in the oral dosage form than a similar dosage form intended to treat sexual dysfunction in females. With this in mind, in one embodiment, the oral dosage forms of the present invention can include testosterone undecanoate in an amount of about 0.5 mg to about 750 mg. In another embodiment, the solid oral dosage form, wherein the testosterone undecanoate is present in an amount of about 1 mg to about 500 mg. In another embodiment, the solid oral dosage form, wherein the testosterone undecanoate is present in an amount of about 5 mg to about 400 mg. In another embodiment, the testosterone undecanoate can be present in the oral dosage form in an amount of about 10 mg to about 250 mg.

In one aspect the solid oral dosage form can be formulated for administration to a human male and the testosterone undecanoate is present in an amount of about 50 mg to about 750 mg. In one embodiment, the solid oral dosage form is formulated for administration to a human male and the testosterone undecanoate is present in an amount of about 75 mg to about 600 mg. In another embodiment, the solid oral dosage form is formulated for administration to a human male and the testosterone undecanoate is present in an amount of about 100 mg to about 400 mg. In yet another aspect, the solid oral dosage form is formulated for administration to a human female and the testosterone undecanoate is present in an amount of about 0.5 mg to about 200 mg. In one embodiment, the solid oral dosage form is formulated for administration to a human female and the testosterone undecanoate is present in an amount of about 1 mg to about 100 mg. In another embodiment, the solid oral dosage form is formulated for administration to a human female and the testosterone undecanoate is present in an amount of about 2 mg to about 50 mg.

The testosterone undecanoate can be present in the solid composition, or oral dosage form, in the crystalline or amorphous form or combinations thereof. In another embodiment, the testosterone undecanoate can be controlled precipitated, milled, micronized or nanosized, or combination thereof. In another embodiment, the testosterone undecanoate can have a mean particle diameter of about 50 µm or less. In another embodiment, the testosterone undecanoate can have a mean particle diameter of about 40 µm or less. In another embodiment, the testosterone undecanoate can have a mean particle diameter of about 30 µm or less. In another embodiment, the testosterone undecanoate can have a mean particle diameter of about 20 µm or less. In another embodiment, the testosterone undecanoate can have a mean particle diameter of about 10 µm or less. In another embodiment, the testosterone undecanoate can have a mean particle diameter of about 5 µm or less. In another embodiment, the testosterone undecanoate can have a mean particle diameter of about 2 µm or less. In another embodiment, the testosterone undecanoate can have a mean particle diameter of about 200 nm or less.

The testosterone undecanoate can be present in the solid oral dosage form as solid particulates. In one embodiment, the solid particulates are not solubilized in the carrier present in oral dosage form. In one embodiment, the solid particulates of testosterone undecanoate can comprise 5% (w/w) or more of the testosterone undecanoate present in the oral dosage form. In one embodiment, the solid particulates of testosterone undecanoate can comprise 15% (w/w) or more of the testosterone undecanoate present in the oral dosage form. In another embodiment, the solid particulates of testosterone undecanoate can comprise 30% (w/w) or more of the testosterone undecanoate present in the oral dosage form. In another embodiment, the solid particulates of testosterone undecanoate can comprise 50% (w/w) or more of the testosterone undecanoate present in the oral dosage form. In another embodiment, the solid particulates of testosterone undecanoate can comprise 70% (w/w) or more of the testosterone undecanoate present in the oral dosage form. In another embodiment, the solid particulates of testosterone undecanoate can comprise 90% (w/w) or more of the testosterone undecanoate present in the oral dosage form.

In one embodiment, the testosterone undecanoate can be present in or on particles having effective average particle sizes of less than 2000 nm or less in diameter. The particles can have at least one surface stabilizer that can be adsorbed on or associated with the surface of the particles having the testosterone undecanoate, or polymorph thereof. Preferably, the surface stabilizer adheres onto, or associates with, the surface of the particles, but does not react chemically with the particles or with other surface stabilizer molecules. Individually adsorbed molecules of the surface stabilizer are essentially free of intermolecular cross-linkages. The relative amounts of the testosterone undecanoate, or polymorph thereof, and surface stabilizer present in the composition of the present invention can vary widely. The amount of the individual components can depend upon, among other things, the particular polymorph selected, the hydrophilic-lipophilic balance (HLB), the melting point, and the surface tension of water solutions of the stabilizer. The concentration of the testosterone undecanoate, or polymorph thereof, can vary from about 99.5% to about 0.001%, from about 95% to about 0.1%, or from about 90% to about 0.5%, by weight, based on the total combined weight of the testosterone undecanoate, or polymorph thereof, and the surface stabilizer(s), not including other excipients. Likewise, the concentration of the surface stabilizer(s) can vary from about 0.5% to about 99.999%, from about 5.0% to about 99.9%, or from about 10% to about 99.5%, by weight, based on the total combined dry weight of the testosterone undecanoate, or polymorph thereof, and surface stabilizer(s), not including other excipients.

It has been discovered that solid oral dosage forms can be formulated to provide the required drug release and bioavailability when appropriate carrier is selected. The amount of the pharmaceutically acceptable carrier used in the oral dosage form can vary depending on factors such as the amount of testosterone undecanoate present in the oral dosage form. In one embodiment, the solid oral dosage form can have an amount of testosterone undecanoate to amount of pharmaceutically acceptable carrier ratio of about 8:1 (w/w) to about 1:8 (w/w). In another embodiment, the solid oral dosage form can have an amount of testosterone undecanoate to amount of pharmaceutically acceptable carrier ratio of about 4:1 (w/w) to about 1:4 (w/w). In another embodiment, the solid oral dosage form can have an amount of testosterone undecanoate to amount of pharmaceutically acceptable carrier ratio of about 2:1 (w/w) to about 1:2 (w/w).

The pharmaceutically acceptable carriers that are included in the oral dosage forms of the present invention can act to facilitate the bioavailability of the testosterone undecanoate. In one embodiment, the pharmaceutically acceptable carrier can include hydrophilic additives, lipophilic additives, or combinations thereof. In one embodiment, the hydrophilic additive is not a hydrophilic surfactant. In another embodiment, the lipophilic additive is not a lipophilic surfactant. In another embodiment, the composition is free of triglyceride, animal and vegetable oils.

In another embodiment, the carrier can be free of hydrophilic surfactants. In another embodiment, the formulation can include a hydrophilic surfactant that does not or does not substantially contribute to the solubility of the testosterone undecanoate within the composition. It is noteworthy, that the phrase "substantially contribute" as it refers to the hydrophilic surfactant's effect on the testosterone undecanoate's solubility refers to the hydrophilic surfactant solubilizing less than 10 wt % of the testosterone undecanoate. In one embodiment, substantially contributes refers to the hydrophilic surfactant solubilizing less than 5 wt % of the testosterone undecanoate. In one embodiment, substantially contributes refers to the hydrophilic surfactant solubilizing less than 1 wt % of the testosterone undecanoate. In other embodiment the hydrophilic surfactant does not solubilize testosterone undecanoate. In another embodiment the carrier is not a hydrophilic surfactant.

The oral dosage forms may also be free of oils. As used herein, the term "oils" refers to pharmaceutically acceptable glycerides that have a triglyceride content of at least 40 wt %. Similarly, another embodiment of the invention provides for the oral dosage form to be free of triglycerides. In one embodiment, the pharmaceutically acceptable carrier in the dosage form is not a lipid substance.

Non-limiting examples of pharmaceutically acceptable carriers can include methyl cellulose; ethyl cellulose; non-crystalline cellulose; microcrystalline cellulose; hypromellose (hydroxypropyl methylcellulose, for example, Methocel, having a viscosity range from 2 to about 140000 cPs); hydroxyethyl cellulose; hydroxypropyl cellulose; carboxymethylcellulose or its salts or combinations thereof; dextrose; cellulose acetate; cellulose acetate pthalate; cellulose acetate butyrate; cellulose acetate trimellitate; cellulose nitrate; carbomers; croscarmellose; cyclodextrins; β-cyclodextrins; α-cyclodextrin; dextrates; sorbitol; lactose; sucrose; maltose; galactose; polyvinylpyrrolidone (povidone K12 to K120); crospovidone; polyvinyl alcohol; glycerol; glucose; polyols; such as mannitol; xylitol or sorbitol or their combinations; polyethylene glycol esters; alginates; sodium alginate; poly(lactide coglycolide); gelatin; cross-linked gelatin; agar-agar; sodium dodecyl sulfate; polyethylene glycols of mol wt range from about 100 to about 20,000 or their mixtures; guar gum; xanthan gum; starches; gum arabic; dextrins; dibasic calcium phosphate; sodium starch glycolate; croscarmellose sodium; galactomannan; tricalcium phosphate; maltodextrin or its derivatives and their combinations; polyoxyethylene stearate; carnuaba wax; poloxamers; deoxycholic acid; polyoxyl sorbitan derivatives; polysorbate; lauroyl macrogolglycerides; polyoxylglycerides; fatty alcohols; sugar esters; sugar ethers; shellacs; tocopherol; tocopherol polyethyleneglycol succinate; tocopherol succinate; tocopherol acetate; pentaerythritol; urea; stearic acid; stearic acid salts; hydroxystearic acid urethane; hydroxyalkyl xanthines; carrageenan; chitosan; benzyl alcohol; ethyl alcohol; cetyl alcohol; cetosterayl alcohol; polycaprolactone; polylactic acid; polyglycolic acid; polylactide-co-glycolides; talc; magnesium stearate; fumed silica; micronized silica; hydrogenated vegetable oils; capric acid; caprylic acid; undecanoic acid; oleic acid;

linoleic acid; eicosapentaenoic acid; docosahexanoic acid; caprylic/capric mono and/or diglycerides; caprylic/capric triglyceride; caprylic/capric/lauric triglyceride; caprylocaproyl macrogolglycerides; oleoyl macrogolglycerides; corn glycerides; corn oil monoglycerides; mono-diglycerides of corn oil, coconut oil, safflower oil, sunflower oil, maize oil; or mixtures thereof; glyceryl monolinoleate; glyceryl stearate; glyceryl palmitostearate; glyceryl oleate; hydrogenated castor oils; medium and/or long chain mono-, di- or triglycerides; sodium benzoate; sodium acetate; acetylated monoglycerides; long-chain alcohols and silicone derivatives; gallic acid; propyl gallate; ascorbic acid; ascorbyl palmitate; bentonite; vinyl pyrrolidone copolymers; hydrochloric acid; phosphoric acid; sulfuric acid; nitric acid; acetic acid; citric acid; tartaric acid; succinic acid; boric acid; phosphoric acid; acrylic acid; adipic acid; alginic acid, alkanesulfonic acid, amino acids, benzoic acid, butyric acid, carbonic acid, fatty acids, formic acid, fumaric acid, gluconic acid, isoascorbic acid, lactic acid, maleic acid, methanesulfonic acid, oxalic acid, propionic acid, salicylic acid, tannic acid, thioglycolic acid, toluenesulfonic acid; uric acid; amino acid ester; ammonium hydroxide, potassium hydroxide, sodium hydroxide, sodium hydrogen carbonate, aluminum hydroxide, magnesium hydroxide; magnesium aluminum hydroxide; magnesium aluminum silicate, synthetic aluminum silicate, synthetic hydrotalcite, diisopropylethylamine, ethanolamine, ethylenediamine, triethanolamine, triethylamine, triisopropanolamine, or a salt of a ethylenediaminetetraacetic acid and its salts; titanium dioxide, food dyes, lakes, natural vegetable colorants, iron oxides, silicates, sulfates, aluminum hydroxidecitric acid, sodium chloride, potassium chloride, calcium sulfate, magnesium oxide, essential oils and ethyl vanillin; styrene/divinyl benzene copolymers, quaternary ammonium compounds, triethyl citrate, acetyl triethyl citrate, acetyltributyl citrate, propylene glycol, phthalate esters (e.g., diethyl phthalate, dibutyl phthalate), castor oil, sorbitol and dibutyl seccateascorbic acid, sorbic acid, parabens, phenols, butylated hydroxyanisole, butylated hydroxytoluene, proteins (e.g., collagen, Zein, gluten, mussel protein, lipoprotein), glycerol fatty acid esters; acetylated glycerol fatty acid esters; lower alcohol fatty acids esters; polyethylene glycol fatty acids esters; polypropylene glycol fatty acid esters; polyoxyethylene glycerides lactic acid esters of mono/diglycerides; propylene glycol diglycerides; polyoxyethylene alkylethers; polyoxyethylene-polyoxypropylene block copolymers such as poloxamer—108, 188, 217, 238, 288, 338, 407, 124, 182, 183, 212, 331, or 335, or combinations thereof; trans-esterified vegetable oils; sterols; cholesterol; sterol derivatives; sucroglycerides; polyoxyethylene vegetable oils; and polyoxyethylene hydrogenated vegetable oils, lecithins, phospholipids, sodium docusate; dioctyl sulfosuccinate; acyl lactylates; mono- and diacetylated tartaric acid esters of mono- and diglycerides; succinylated monoglycerides, paraffin oil, paraffin wax, silicone oil, dimethicone, simethicone, silicon dioxide, macrogol 15 hydroxystearate (Solutol), sucrose acetate isobutyrate, polyethoxylated cholesterol; stearoyl polyoxyglycerides; acrylic acid polymers such as methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, polyacrylamide, glycidyl methacrylate copolymers, and combinations thereof.

In one embodiment, the pharmaceutically acceptable carrier can include at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxyl propyl methyl cellulose; ethyl cellulose; carbomers; gelatin; poloxamers; sodium dodecyl sulfate; sodium docusate; sorbitan esters, polyoxyethylene sorbitan esters; glycerin; paraffin oil; silicone oils; magnesium aluminosilicates; silicon dioxide; ethyl alcohol; benzyl alcohol; benzyl benzoate; ascorbic acid; oleic acid; linoleic acid; stearic acid; capric acid; caprylic acid; caprylic/capric fatty acid mono and/or diglycerides; hydrogenated castor oil; corn oil macrogolglycerides; linoleic/oleic fatty acid mono- and/or diglycerides; caprylocaproyl macrogolglycerides; mono- and/or diglycerides of coconut oil or maize oil or safflower oil or sunflower oil or mixtures thereof; glycerol esters of saturated $C_{12}$-$C_{18}$ fatty acid; glyceryl monostearate; glyceryl distearate; glyceryl palmitostearate; glyceryl behenate; glyceryl monolinoleate; triglycerides; oils; fatty acids; triethyl citrate; linoleoyl macrogolglycerides, lauroyl macrogolglycerides; sugar esters; acetylated mono- and/or diglycerides; stearoyl polyoxyglycerides; trans-esterified vegetable oils; lecithin; phospholipids; polyethoxylated cholesterol; glyceryl oleate, cholesterol; tocopherol; tocopherol succinate; medium and/or long chain mono-, diglycerides; polyoxyl castor oils or mixtures thereof.

In another embodiment, the pharmaceutically acceptable carrier can include at least one of polyvinyl alcohol, polyvinyl pyrrolidones, polyethylene glycols having molecular weight from about 100 to about 20,000; cyclodextrins; maltodextrin; hydroxylpropyl methyl cellulose; carbomers; gelatin; poloxamers; sodium dodecyl sulfate; sodium docusate; sorbitan esters, polyoxyethylene sorbitan esters; ethyl alcohol; benzyl alcohol; benzyl benzoate; oleic acid; linoleic acid; stearic acid; capric acid; caprylic acid; caprylocaproyl macrogolglycerides; corn oil macrogolglycerides; glyceryl monostearate; glyceryl distearate; glyceryl palmitostearate; glyceryl monolinoleate; cholesterol; tocopherol; polyoxyl vegetable oils; triethyl citrate; linoleoyl macrogolglycerides, lauroyl macrogolglycerides; sugar esters; stearoyl polyoxyglycerides; lecithin; phospholipids; polyethoxylated cholesterol; or mixtures thereof.

In another embodiment, the pharmaceutically acceptable carrier can include at least one of polyvinyl alcohol, polyvinyl pyrrolidones, polyethylene glycols having molecular weight from about 100 to about 20,000; cyclodextrins; maltodextrin; hydroxylpropyl methyl cellulose; carbomers; gelatin; poloxamers; sodium dodecyl sulfate; sodium docusate; polyoxyethylene sorbitan esters; ethyl alcohol; benzyl alcohol; benzyl benzoate; caprylocaproyl macrogolglycerides; corn oil macrogolglycerides; polyoxyl castor oils; polyoxyl vegetable oils; triethyl citrate; linoleoyl macrogolglycerides, lauroyl macrogolglycerides; sugar esters; stearoyl polyoxyglycerides; or mixtures thereof.

In another embodiment, the pharmaceutically acceptable carrier can include at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose; hydroxyl propyl methyl cellulose; ethyl cellulose; carbomers; gelatin; sorbitan esters; glycerin; paraffin oil; silicone oils; magnesium aluminosilicates; silicon dioxide; ethyl alcohol; benzyl alcohol; benzyl benzoate; ascorbic acid; oleic acid; linoleic acid; stearic acid; capric acid; caprylic acid; caprylic/capric mono and/or diglycerides; hydrogenated castor oil; mono- and/or diglycerides of coconut oil or, maize oil, safflower oil, sunflower oil, or mixtures thereof; glyceryl monostearate; glyceryl distearate; glyceryl palmitostearate; glyceryl behenate; glyceryl mono-linoleate; glyceryl oleate, cholesterol; tocopherol; tocopherol succinate; medium and/or long chain mono-, diglycerides; fatty acids; triethyl citrate; linoleoyl macrogolglycerides, lauroyl macrogolglycerides; sugar esters; acetylated mono- and/or diglycerides; steroyl polyoxyglycerides; trans-esterified vegetable oils; lecithin; phospholipids; or mixtures thereof.

In another embodiment, the pharmaceutically acceptable carrier can include at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxyl propyl methyl cellulose; ethyl cellulose; carbomers; gelatin; poloxamers; sodium dodecyl sulfate; sodium docusate; polyoxyethylene sorbitan esters; glycerin; paraffin oil; silicone oils; magnesium aluminosilicates; silicon dioxide; ethyl alcohol; benzyl alcohol; benzyl benzoate; ascorbic acid; oleic acid; linoleic acid; stearic acid; capric acid; caprylic acid; hydrogenated castor oil; caprylocaproyl macrogolglycerides; cholesterol; tocopherol; tocopherol succinate; polyoxyl castor oils; polyethoxylated cholesterol or mixtures thereof.

In another embodiment, the preferred pharmaceutically acceptable carrier is free of lipophilic additives and can include at least one of polyvinyl alcohol, polyvinyl pyrrolidones, polyethylene glycols having molecular weight from about 100 to about 20,000; cyclodextrins; maltodextrin; hydroxylpropyl methyl cellulose; carbomers; gelatin; poloxamers; sodium dodecyl sulfate; sodium docusate; polyoxyethylene sorbitan esters; ethyl alcohol; benzyl alcohol; benzyl benzoate; caprylocaproyl macrogolglycerides; polyoxyl castor oils; polyoxyl vegetable oils; triethyl citrate; lauroyl macrogolglycerides; sugar esters; stearoyl polyoxyglycerides or mixtures thereof.

In yet another embodiment, the pharmaceutically acceptable carrier is free of hydrophilic surfactants and includes at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxylpropyl methyl cellulose; ethyl cellulose; carbomers; gelatin; sorbitan esters, glycerin; paraffin oil; silicone oils; magnesium aluminosilicates; silicon dioxide; ethyl alcohol; benzyl alcohol; benzyl benzoate; ascorbic acid; oleic acid; linoleic acid; stearic acid; capric acid; caprylic acid; caprylic/capric mono and/or diglycerides; hydrogenated castor oil; mono- and/or diglycerides of coconut oil or, maize oil, safflower oil, sunflower oil, or mixtures thereof; glyceryl monostearate; glyceryl distearate; glyceryl palmitostearate; glyceryl behenate; glyceryl monolinoleate; glyceryl oleate, cholesterol; tocopherol; tocopherol succinate; medium and/or long chain mono-, diglycerides; fatty acids; triethyl citrate; linoleoyl macrogolglyceride; lauroyl macrogolglycerides; sugar esters; acetylated mono- and/or diglycerides; steroyl polyoxyglycerides; trans-esterfied vegetable oils; lecithin; phospholipids; or mixtures thereof.

In another embodiment, the pharmaceutically acceptable carrier is free of lipophilic surfactants and includes at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxylpropyl methyl cellulose; ethyl cellulose; carbomers; gelatin; poloxamers; sodium dodecyl sulfate; sodium docusate; polyoxyethylene sorbitan esters; glycerin; paraffin oil; silicone oils; magnesium aluminosilicates; silicon dioxide; ethyl alcohol; benzyl alcohol; benzyl benzoate; ascorbic acid; oleic acid; linoleic acid; stearic acid; capric acid; caprylic acid; hydrogenated castor oil; caprylocaproyl macrogolglycerides; cholesterol; tocopherol; tocopherol succinate; polyoxyl castor oils; polyethoxylated cholesterol or mixtures thereof.

In another embodiment, the pharmaceutically acceptable carrier is free of lipid substance and includes at least one of polyvinyl alcohol, polyvinyl pyrrolidones, polyethylene glycols having molecular weight from about 100 to about 20,000; cyclodextrins; maltodextrin; hydroxylpropyl methyl cellulose; carbomers; gelatin; poloxamers; ethyl alcohol; benzyl alcohol; benzyl benzoate or combinations thereof.

In yet another embodiment, the pharmaceutically acceptable carrier can include polyvinyl alcohol, polyvinyl pyrrolidones, polyethylene glycols having molecular weight from about 1000 to about 20,000, or combination thereof. In a further embodiment, the solid composition of the current invention includes less than 30 wt % of polyethylene glycol. In a particular embodiment, the solid composition of the current invention includes from about 0.1 wt % to about 27 wt % of polyethylene glycol. In another embodiment, the solid composition of the current invention includes from about 3 wt % to about 20 wt % of polyethylene glycol. In another particular embodiment, the solid composition of the current invention can include from about 6 wt % to about 15 wt % of polyethylene glycol.

In a further embodiment, the solid composition or dosage form of the current invention includes about 45% or less of a lipid substance. In a further embodiment, the solid composition or dosage form includes about 30% or less of a lipid substance. In a further embodiment, the solid composition or dosage form includes about 15% or less of a lipid substance. In a further embodiment, the solid composition or dosage form includes about 5% or less of a lipid substance. In another particular embodiment, the solid composition or dosage form is free of lipid substance. In another embodiment, the pharmaceutical carrier in the dosage form does not include a lipid substance with chain length greater than $C_{12}$.

The solid oral dosage forms are capable of providing adequate in vivo bioavailability to provide therapeutic effect for testosterone therapy of both female and male subjects. In one aspect of the invention, the oral dosage form can be formulated to have a delayed release such that the testosterone undecanoate does not have any release, or any significant (not more than 10 wt %) release, in the first 15 minutes following administration. It has been discovered that by delaying the initial release of the testosterone undecanoate for this time period, the oral dosage form provides a pharmacokinetic profile that may be more acceptable than when the testosterone undecanoate is allowed to release immediately.

With this in mind, the solid oral dosage forms of the present invention can be formulated to release about 85 wt % or less of the testosterone undecanoate in the first 30 minutes following administration to a subject. In one embodiment, the solid oral dosage form can release less than 70 wt % of the testosterone undecanoate in the first 30 minutes following administration. In another embodiment, the solid oral dosage form can be formulated to release at least 35 wt % of the testosterone undecanoate in the first 120 minutes following administration to a human subject. In another embodiment, the solid oral dosage form can be formulated to release at least 45 wt % of the testosterone undecanoate in the first 120 minutes following administration to a human subject. In yet a further embodiment, the solid oral dosage form can be formulated to release at least about 50 wt % in the first 120 minutes following administration to a human subject.

As discussed above, the solid oral dosage forms of the present invention provide adequate bioavailability of the testosterone undecanoate so as to generate therapeutically effective pharmacokinetic levels of testosterone undecanoate and testosterone, without the need to administer excessive amounts of the active agent. In one embodiment, the dosage form when administered to a human male the oral dosage provides a dose to plasma total testosterone $C_{avg}$ ratio of $4.5 \times 10^4$ dL to $4 \times 10^6$ dL. In another embodiment, the dosage form when administered to a human male the oral dosage provides a dose to plasma total testosterone $C_{avg}$ ratio of $6 \times 10^4$ dL to $3 \times 10^6$ dL. In another embodiment, the dosage form when administered to a human male, the oral dosage provides a dose to plasma testosterone $C_{avg}$ ratio of $9 \times 10^4$ dL to $2 \times 10^6$ dL.

In one embodiment, the dosage form when administered to a human female, the oral dosage provides a dose to plasma total testosterone $C_{avg}$ ratio of $5 \times 10^3$ dL to $2 \times 10^7$. In another embodiment, the dosage form when administered to a human female, the oral dosage provides a dose to plasma total testosterone $C_{avg}$ ratio of $1 \times 10^4$ dL to $1 \times 10^7$ dL. In another embodiment, the dosage form when administered to a human female, the oral dosage provides a dose to plasma total testosterone $C_{avg}$ ratio of $2 \times 10^4$ dL to $5 \times 10^6$ dL.

In one embodiment, the oral dosage form, when after administration to a human male, can provide a plasma total testosterone $C_{avg}$ of about 300 ng/dL to about 1100 ng/dL. In another embodiment, the oral dosage form, when after administrations to a human male, can provide a plasma total testosterone $C_{avg}$ of about 350 ng/dL to about 800 ng/dL. In another embodiment, the oral dosage form, when after administrations to a human male, can provide a plasma total testosterone $C_{avg}$ of about 400 ng/dL to about 600 ng/dL. In yet another embodiment, the oral dosage form, when after administrations to a human male, the oral dosage form provides a plasma total testosterone undecanoate $C_{avg}$ of about 1.5 ng/mL to about 1 µg/mL. In another embodiment, the oral dosage form, when after administrations to a human male, can provide a plasma total testosterone undecanoate $C_{avg}$ of about 10 ng/mL to about 850 ng/mL.

When administered to a human female, the oral dosage forms of the present invention can be formulated to provide a plasma total testosterone $C_{avg}$ of about 1 ng/dL to about 100 ng/dL. In another embodiment, when administered to a human female, the oral dosage form can provide a plasma total testosterone $C_{avg}$ of about 20 ng/dL to about 80 ng/dL. In yet a further embodiment, when administered to a human female, the oral dosage form can provide a plasma total testosterone $C_{avg}$ of about 30 ng/dL to about 70 ng/dL.

In a further embodiment, the dosage forms can be formulated such that when administered to a human subject, provides a ratio of serum testosterone undecanoate $C_{avg}$ to serum total testosterone $C_{avg}$ of about 3:1 to about 100:1. In a further embodiment, the dosage forms can be formulated such that when administered to a human subject, provides a ratio of serum testosterone undecanoate $C_{avg}$ to serum total testosterone $C_{avg}$ of about 4:1 to about 50:1.

In one embodiment, a single dose of the testosterone undecanoate composition or oral dosage form can provide a $C_{avg}$ for testosterone of about 300 ng/dL or more from about 0.5 hours to about 24 hours after oral administration with a meal. In a further embodiment, a single dose of a testosterone undecanoate composition or oral dosage form can provide a $C_{avg}$ for plasma total testosterone of about 300 ng/dL or more at about 20 hours after oral administration with a meal. In yet a further embodiment, a single dose of the testosterone undecanoate composition can provide a $C_{avg}$ for plasma total testosterone of about 300 ng/dL or more at about 18 hours after oral administration with a meal. In still a further embodiment, a single dose of the testosterone undecanoate oral dosage form can provide a $C_{avg}$ for plasma total testosterone of about 300 ng/dL or more at about 16 hours after oral administration with a meal. In still a further embodiment, a single dose of the testosterone undecanoate oral dosage form can provide a $C_{avg}$ for plasma total testosterone of about 300 ng/dL or more at about 12 hours after administration after oral administration with a meal. In still a further embodiment, a single dose of the testosterone undecanoate oral dosage form can provide a $C_{avg}$ for plasma total testosterone of about 300 ng/dL or more at about 8 hours after oral administration with a meal. The meal that is administered with the composition or oral dosage form can be a standard meal (comprising about 30 g to about 35 g fat).

In another embodiment, a pharmaceutical oral dosage form, when administered once daily, provides a plasma total testosterone $C_{avg}$ of about 300 ng/dL to 700 ng/dL. In another embodiment, a pharmaceutical oral dosage form, when administered once daily, provides a plasma total testosterone $C_{avg}$ of about 300 ng/dL to 600 ng/dL.

In one embodiment, the pharmaceutical oral dosage form can, when administered twice daily (e.g. once every 12 hours), provide a plasma total testosterone $C_{avg}$ of about 300 ng/dL to 1000 ng/dL. In another embodiment, the pharmaceutical oral dosage form can, when administered twice daily, provide a plasma total testosterone $C_{avg}$ of about 350 ng/dL to 800 ng/dL. In another embodiment, the pharmaceutical oral dosage form can, when administered twice daily, provide a plasma total testosterone $C_{avg}$ of about 400 ng/dL to 600 ng/dL. In another embodiment, the pharmaceutical oral dosage form can, when administered twice daily, provide a plasma total testosterone $C_{avg}$ of about 300 ng/dL to 1000 ng/dL. In another embodiment, the pharmaceutical oral form, when administered twice daily such that more than 100 mg testosterone undecanoate is administered during the day and less than 100 mg administered during the night, can provide a plasma total testosterone $C_{avg}$ of about 300 ng/dL to 1000 ng/dL. In another embodiment, the pharmaceutical oral form, when administered twice daily such that more than 100 mg testosterone undecanoate is administered during the day and less than 100 mg administered during the night, can provide a plasma total testosterone $C_{avg}$ of about 300 ng/dL to 800 ng/dL. In another embodiment, the pharmaceutical oral form, when administered twice daily such that more than 100 mg testosterone undecanoate is administered during the day and less than 100 mg administered during the night, can provide a plasma total testosterone $C_{avg}$ of about 400 ng/dL to 700 ng/dL. In another embodiment, the pharmaceutical oral form, when administered twice daily such that more than 100 mg testosterone undecanoate is administered during the day and less than 100 mg administered during the night, can provide a plasma total testosterone $C_{avg}$ of 400 ng/dL to 600 ng/dL.

The oral dosage forms of the present invention can be used to treat testosterone deficiency in post menopausal women. In one embodiment, a pharmaceutical oral dosage form is provided that, when administered once daily to post menopausal women, provides a plasma total testosterone $C_{avg}$ of about 10 ng/dL to 100 ng/dL. In another embodiment, a pharmaceutical oral dosage form is provided that, when administered once daily to post menopausal women, provides a plasma total testosterone $C_{avg}$ of about 20 ng/dL to 60 ng/dL. In another embodiment, a pharmaceutical oral dosage form is provided that, when administered once daily to post menopausal women, provides a plasma total testosterone $C_{avg}$ of about 20 ng/dL to 40 ng/dL The oral dosage forms disclosed herein can also be used to treat testosterone deficiency in pre-menopausal women. In another embodiment, a pharmaceutical oral dosage form is provided that, when administered once daily to pre menopausal women in order to provides, plasma total testosterone $C_{avg}$ of about 10 ng/dL to 100 ng/dL. In another embodiment, a pharmaceutical oral dosage form is provided that, when administered once daily to pre menopausal women in order to provides, plasma total testosterone $C_{avg}$ of about 20 ng/dL to 60 ng/dL. In another embodiment, a pharmaceutical oral dosage form is provided that, when administered once daily to pre menopausal women in order to provides, plasma total testosterone $C_{avg}$ of about 20 ng/dL to 40 ng/dL.

The oral dosage forms may also be used to treat testosterone deficiency in peri-menopausal women as well as in oopherectomized women. In one embodiment, a pharmaceutical oral dosage form is provided that, when administered once daily to peri-menopausal women, provides a plasma total testosterone $C_{avg}$ of about 10 ng/dL to 100 ng/dL. In one embodiment, a pharmaceutical oral dosage form is provided that, when administered once daily to peri-menopausal women, provides a plasma total testosterone $C_{avg}$ of about 20 ng/dL to 60 ng/dL. In one embodiment, a pharmaceutical oral dosage form is provided that, when administered once daily to peri-menopausal women, provides a plasma total testosterone $C_{avg}$ of about 20 ng/dL to 40 ng/dL. In one embodiment, a pharmaceutical oral dosage form is provided that, when administered once daily to oopherectomized women, provides a plasma total testosterone $C_{avg}$ of about 10 ng/dL to 100 ng/dL. In one embodiment, a pharmaceutical oral dosage form is provided that, when administered once daily to oopherectomized women, provides a plasma total testosterone $C_{avg}$ of about 20 ng/dL to 60 ng/dL. In one embodiment, a pharmaceutical oral dosage form is provided that, when administered once daily to oopherectomized women, provides a plasma total testosterone $C_{avg}$ of about 20 ng/dL to 40 ng/dL.

The oral dosage forms of the present invention can be used to treat subjects in need of testosterone therapy, both males and females. In another embodiment, a method of treating a subject in need of testosterone therapy is provided that includes administering to the subject any of the solid oral dosage forms of the present invention. Depending on the particular oral dosage form and the needed therapy, the administration can be done once every 24 hours, once every 12 hours, or once every eight hours. In one embodiment, the administration can include more than one unit of the solid oral dosage form. In one embodiment, the subject can be a human male and the solid oral dosage form provides a daily dose of testosterone undecanoate of about 50 mg to about 1500 mg per day. In another embodiment, the subject can be a human female and the solid oral dosage form can provide a daily dose of testosterone undecanoate of 0.5 to 200 mg per day.

The testosterone undecanoate dosage compositions and oral dosage forms disclosed herein can be orally administered in a 24 hours' dosing regimen (also referred to as or a daily dosing regimen) that is suitable to the needs of the subject. The 24 hours' dosing regimen can include administering the dosage forms after meals in the morning, at about noon, in the evening, at about night time or combinations thereof. The 24 hours' dosing regimen can include dosing one or more dosage units at one or more administration times.

The compositions and oral dosage forms disclosed herein can be orally administered with food without regards to the food or food content. In one embodiment, the oral dosage form can be orally administered without food. In another embodiment, the composition or oral dosage form can be administered with a meal, such as a meal that provides about 200 calories to about 1000 calories of energy. In another embodiment, the composition or oral dosage form can be administered with a meal that provides about 50% of the calories from the fat. In another embodiment, the composition or oral dosage form can be administered with a high-fat, high calorie meal. In another embodiment, the composition or oral dosage form can be administered with a standard meal that provides about 500 calories to about 1000 calories of energy. The compositional make-up of the meals that are administered can vary depending on the tastes and dietary needs of a subject. However, in some situations it may be beneficial to administer the compositions and oral dosage forms with meals that provide no fat to about 50 g of fat. In one embodiment, the meal can provide about 10 g to about 50 g of fat. In yet a further embodiment, the meal can provide 15 g to about 35 g of fat. In one embodiment, when the oral dosage form is administered to a human female, it can be done without regard to the presence of or nutritional make-up of a meal.

In another embodiment, when administering the oral dosage form, the total daily dose of the testosterone undecanoate administered to human subject with standard meal is between about 20% to about 70% of the total daily dose administered without meals, for a similar therapeutic benefit.

It has been surprisingly discovered that the testosterone undecanoate oral dosage forms of the present invention can provide in vitro release of less than about 85% of the testosterone undecanoate in the oral dosage form in the first 30 minutes, and that such release provides, upon a single oral administration with meals to a human subject, about 10% or more testosterone undecanoate AUC as compared to an equivalent dose of testosterone undecanoate in an immediate release dosage capsule administered under same conditions. The in vitro release profile is determined in about 1000 mL of 8% w/v Triton X-100 solution at about 37° C. in an USP Type-2 Apparatus at about 100 rpm. Immediate release dosage forms are dosage forms that release more than 85% of the testosterone undecanoate in the dosage form within the first 30 minutes in the above in vitro release conditions.

In one embodiment, the testosterone undecanoate oral dosage forms of the current invention, when compared to an equivalent dose testosterone undecanoate containing immediate release dosage form, can provide upon a single oral administration with meal to a human subject about 15% or more testosterone undecanoate AUC. In another embodiment, the testosterone undecanoate oral dosage form can provide 10% or more testosterone undecanoate bioavailability as compared to an equivalently dosed immediate release oral dosage form. In another embodiment, the testosterone undecanoate oral dosage form can provide 10% or more reduction in the inter-subject variability of the testosterone undecanoate $C_{max}$, testosterone undecanoate AUC, or both as compared to an equivalently dosed immediate release oral dosage form. In another embodiment, the testosterone undecanoate oral dosage form can provide 10% or more testosterone exposure or bioavailability in subjects as compared to equivalent dosed immediate release oral dosage forms. In another embodiment, the testosterone undecanoate oral dosage form can provide 10% or more reduction in the variability of plasma total testosterone $C_{max}$, testosterone AUC, or both.

The need for testosterone therapy can be associated with a variety of conditions, and thus the oral dosage forms of the present invention can be used to treat a variety of conditions. Generally, the compositions and oral dosage forms of the present invention can be used to treat any condition associated with testosterone deficiency, including complete absence, of endogenous testosterone. In one embodiment, the subject can be a male and the need for testosterone therapy can be associated with a condition selected from the group consisting of hygonadism; erectile dysfunction; Klienfelter Syndrome; reduced libido; low muscle mass, and low bone density; metabolic syndrome, and combinations thereof.

In another embodiment, the subject can be a human female and the need for testosterone therapy can be associated with a condition selected from the group consisting of hypoactive sexual desire disorder, arousal disorder, dyspareunia, anorgasmia, and combinations thereof. In further embodiments, the oral dosage form of the present disclosure can be administered to menopausal women to can achieve one or more of the following: increase their sexual desire, increase their sexual activity, increase their libido, increase their sexual fantasy, increase satisfaction in their sexual activity, increase their subjective quality of sexual acts, increase their frequency of sexual thoughts, increase their self reported mood, increase their self reported energy, increase their bone mineral density, increase their cognitive function, treat their hormone-related depression, treat their arousal disorder, or treat their hypoactive sexual disorder.

Other examples of conditions associated with testosterone deficiency that can also be treated using the oral dosage capsules and/or compositions of the present invention are also provided below. It is understood that some of the conditions are gender specific while others may be treated in both genders. Knowledge of such conditions is well within the knowledge of own of ordinary skill in the art. With this in mind, additional conditions that can be treated with the compositions and oral dosage forms of the present invention include, but are not limited to congenital or acquired primary hypogonadism, hypogonadotropic hypogonadism, cryptorchidism, bilateral torsion, orchitis, vanishing testis syndrome, orchidectomy, Klinefelter's syndrome, post castration, eunuchoidism, hypopituitarism, endocrine impotence, infertility due to spermatogenic disorders, impotence, male sexual dysfunction (MSD) including conditions such as premature ejaculation; erectile dysfunction, decreased libido, and the like, micropenis and constitutional delay, penile enlargement, appetite stimulation, testosterone deficiency associated with chemotherapy, testosterone deficiency associated with toxic damage from alcohol, testosterone deficiency associated with toxic damage from heavy metal, osteoporosis associated with androgen deficiency, hot flashes, dry and thin skin, weight gain, and combinations thereof.

Other conditions that can be treated by the compositions and oral dosage forms disclosed herein include idiopathic gonadotropin, LHRH deficiency, or pituitary hypothalamic injury from tumors, trauma, or radiation. Typically, these subjects have low serum testosterone levels but have gonadotropins in the normal or low range. In one embodiment, the compositions or oral dosage forms may be used to stimulate puberty in carefully selected males with clearly delayed puberty not secondary to pathological disorder. In another embodiment, the compositions and oral dosage forms may be used in female-to-male transsexuals in order to maintain or restore male physical and sexual characteristics including body muscle mass, muscle tone, bone density, body mass index (BMI), enhanced energy, motivation and endurance, restoring psychosexual activity etc. In some embodiments, the testosterone undecanoate compositions and oral dosage capsules may be useful in providing hormonal male contraception. Additionally, testosterone therapy can also be used to improve the quality of life of subjects suffering for conditions such as decreased libido, anemia due to marrow failure, renal failure, chronic respiratory or cardiac failure, steroid-dependent autoimmune disease, muscle wasting associated with various diseases such as AIDS, preventing attacks of hereditary angioedema or urticaria; andropause, and palliating terminal breast cancer. In some situations, certain biomarkers such as for example, increased SHBG levels, can be used to diagnose a subject who may be in need of testosterone therapy. These biomarkers can be associated with conditions/disease states such as anorexia nervosa, hyperthyroidism, hypogonadism, androgen insensitivity/deficiency, alcoholic hepatic cirrhosis, primary biliary cirrhosis, and the like.

Subjects that can be treated by the testosterone undecanoate compositions and oral dosage capsule of the present disclosure can be any male or female in need thereof. In particular, in one embodiment, the human male may be at least 14 years of age. In another embodiment, the human male is an adult of at least age 30. In a further embodiment, the subject can be an adult male of at least age 50. In yet a further embodiment, the subject can be an adult male of at least age 60.

As discussed above, the compositions and oral dosage forms disclosed herein can be used to treat testosterone deficiency in human males. In one embodiment, the human male being treated can have an average baseline plasma testosterone concentration (T-$C_{avg\text{-}B}$) of about 400 ng/dL or less. In another embodiment, the human male being treated can have an average baseline plasma testosterone concentration of about 350 ng/dL or less. In another embodiment, the human male being treated can have an average baseline plasma testosterone concentration of about 300 ng/dL or less. In another embodiment, the human male being treated can have an average baseline plasma testosterone concentration of about 250 ng/dL or less. In still another embodiment, the human male being treated can have an average baseline plasma testosterone concentration of about of about 190 ng/dL or less. In still a further embodiment, the human male has an average baseline plasma testosterone concentration (T-$C_{avg\text{-}B}$) of about 400 ng/dL or less, along with a co-morbid condition of insulin resistance.

Further, there are several biomarkers that can be used to identify patients who need testosterone therapy. Accordingly, in one embodiment, the human male being treated can have a low density lipoproteins (LDL) level in greater than about 130 mg/dL of blood. In another embodiment, the human male being treated can have a high density lipoproteins (HDL) level less than about 40 mg/dL of blood. In still another embodiment, the human male being treated can have a total cholesterol level greater than about 220 mg/dL of blood. In yet a further embodiment, the human male being treated can have an average TG (triglycerides) levels greater than 250 mg/dL of blood. In one embodiment, the testosterone undecanoate dosage forms of the current invention can be administered to human male whose bioavailable or free or un-bound plasma estradiol levels are about 20 pg/mL or less. In another embodiment, dosage forms of the current invention can be administered to human male who has a ratio of the bioavailable or free or unbound plasma testosterone level to the bioavailable or free or un-bound plasma estradiol level at about 100 or less.

The testosterone undecanoate compositions and oral dosage forms of the current invention can be administered orally to a human male who has an average body mass index (BMI) of about 30 kg/m$^2$ or more. In another embodiment, the human male has an average BMI of about 37 kg/m$^2$ or more. In a further embodiment, the subject male being treated can have a serum sex hormone binding globulin (SHBG) levels of about 40 nmol/L or more. In yet still another embodiment, the human male being treated can have a serum SHBG levels of about 60 nmol/L or more.

The compositions and associated oral dosage forms of the present invention can be used in conjunction with or as a component of a diagnostic or treatment kit that enables diagnosis and treatment of patients in need of testosterone therapy. The diagnostic or treatment kit may comprise one or more testosterone undecanoate compositions or oral dosage forms with one or more other components, including, but not limited to 1) instructions to enable those ordinarily skilled in the art to prepare a dosage form for immediate dispensing to the subject in need of; 2) one or more containers filled with one or more of the ingredients of the oral pharmaceutical dosage forms of the invention. Suitable containers include, for example, a bottle, a box, a blister card, a foil packet, or a combination thereof; 3) a tamper proof container or packaging; 4) other pharmaceutical dosage forms including other active agents including estrogens, progesterones, PDE-5 inhibitors and glucocorticosteroids; 5) Notice or printed instructions: in a form prescribed by a governmental agency regulating the manufacture, use, or sale of pharmaceuticals or biological products, which notice reflects approval by the agency of the manufacture, use, or sale for human administration to treat a condition that could be treated by oral testosterone therapy; 6) A "planner" for monitoring and tracking administration of the oral dosage forms; 7) Containers for storing and transporting the components of the kit. 8) total testosterone or free testosterone testing kits 9) Sex Hormone binding globulin, SHBG, testing kits 10) Body mass index testing materials to identify high risk patients; 11) tests for identifying patients with hypogonadism 12) tests to assess testicular function or impotency 13) test for bone mineral density/osteoporosis 14) test for hair density 15) test for muscle mass and strength 16) test for determining erectile dysfunction 17) test for decreased libido 18) test for fatigue, depression, mood disorders or irritability 19) test for infertility 20) test for prostate condition 21) test for determining hypoactive sexual desire disorder 22) test for determining mood disorder. 23) test for determining cardiovascular effects 24) test for determining cancers such as breast, uterine, etc.

The oral dosage compositions and oral dosage capsules disclosed herein can be co-administered with other active agents in order to treat a target condition. For example, phosphodiesterase type 5 (PDE-5) inhibitors, such as sildenafil citrate, tadalafil, vardenafil avanafil, lodenafil, mirodenafil, udenafil, and the like, are used to block the degradative action of phosphodiesterase type 5 enzyme on cyclic GMP in the smooth muscle cells lining the blood vessels supplying the corpus cavernosum of the penis and are frequently used to treat erectile dysfunction. Such compounds could be co-administered with the compositions and oral dosage forms of the present invention in order to provide improved clinical outcomes through synergistic pharmacological action as measured by improved (sooner, better and longer lasting) erection, potency, libido, mood, body mass, etc. in males relative to administration of the testosterone or the co-administered PDE-5 alone. The testosterone undecanoate compositions and oral dosage capsules can also be co-administered with one or more other active agents such as aromatase inhibitors (for example letrozole, anastrozole, exemestane, fadrozole, vorozole, formestane etc.), dopamine agonists (for example apomorphine, bromocriptine, cabergoline, pergolide, ropinirole, rotigotine, pramipexole, fenoldopam etc.), prostaglandins (for example alprostadil), alpha blockers (for example yohimbine, phentolamine), vasodilators (for example minoxidil) and the like, for improved clinical outcomes through synergistic pharmacological action as measured by improvements in one or more of the secondary sexual characteristics in males such as sexual activity, potency, libido, erection etc., mood, body mass and the like, relative to administration of either the testosterone or the co-administered active agent alone.

EXAMPLES

The following examples are provided to promote a more clear understanding of certain embodiments of the present invention, and are in no way meant as a limitation thereon. Unless otherwise specified/mentioned, all the compositions provided in the examples are with respect to % w/w of the final composition. Note that, except in the formulations of Examples 1, 6, 9, 16 and 21 the testosterone undecanoate of all other example formulations can be in either treated (milled, micronized, or nanosized) or untreated form. The testosterone undecanoate in formulations 1, 6, 9, 16 and 21 are untreated for size reduction (unmilled, non-micronized, or non-nanosized), and had average particle size greater than 50 micrometer.

Examples 1-5—Testosterone Undecanoate Compositions

Testosterone undecanoate formulations of Examples 1 through 5 were prepared by using the respective components shown in Table I. Example 1 is just crystalline untreated (for example, unmilled or non-micronized, having mean particle size more than 50 micrometer). Testosterone undecanoate filled into a hard gelatin capsule, and Examples 2-5 are prepared as follows: The required quantities of each of the components of the respective formulation, except testosterone undecanoate, are taken in a clean stainless steel container and mixed at about 50° C. to 70° C. using a stirrer. A molten clear-to-hazy mixture is obtained. The required amount of the testosterone undecanoate is added to the clear-to-hazy mixture and stirred to form a homogenous liquid mixture. A predetermined weight of the resulting liquid mixture is disposed into appropriate size capsules according to the testosterone undecanoate dose required.

The capsules were allowed to solidify at room temperature and then banded, and packaged in HDPE bottles and sealed with a tightly closing lid.

Each of the formulations was tested for release of the testosterone undecanoate using a USP Type II apparatus in 1000 mL of 8 wt % Triton X-100 in water at 37° C. and 100 rpm. The percent of the testosterone undecanoate released from each formulation was analyzed using HPLC. The results of the drug release testing are also shown in Table I. It should be noted that the Example 1 (having TU without a carrier) and Example-2 (lipid-based liquid formulation wherein entire TU amount in the dosage unit is solubilized) can be used for comparison purposes to help illustrate the advantages of the solid compositions and dosage forms of the current invention.

TABLE I

| | Composition in % w/w. | | | | |
|---|---|---|---|---|---|
| Ingredients | Example 1 | Example 2 | Example 3 | Example 4 | Example 5 |
| Testosterone Undecanoate | 100 | 12 | 15 | 11 | 18 |
| Triglyceride: Ex: Castor Oil NF | — | 53 | — | 48 | — |
| Lipophilic additive: Ex: Lauroglycol FCC | — | 35 | — | 32 | — |
| Lipophilic additive: Glyceryl Monolinoleate, NF | — | — | 63 | — | 75 |
| Hydrophilic additive: Polyoxyl 40 Hydrogenated Castor Oil, NF | — | — | 16 | — | — |
| Hydrophilic additive: PEG 8000 USP | — | — | 6 | 9 | 7 |
| % release in 30 mins | 12 | 100 | 85 | 67 | 62 |
| % release in 120 mins | 30 | 100 | 101 | 100 | 100 |

Testosterone undecanoate formulations of Examples 6 through 9 can be prepared by using the components shown in Table II. Each of the formulations was tested for release of the testosterone undecanoate using a USP Type II apparatus in 1000 mL of 8 wt % Triton X-100 in water at 37° C. and 100 rpm.

TABLE II

| | Composition in % w/w. | | | |
|---|---|---|---|---|
| Ingredients | Example 6 | Example 7 | Example 8 | Example 9 |
| Testosterone Undecanoate (particle > 50 micrometer) | 90-99 | | | 70 |
| Testosterone Undecanoate micronized or nanosized | — | 90-99 | — | — |
| Testosterone Undecanoate (milled) | — | — | 90-99 | — |
| Lactose | 1-10 | 1-10 | 1-10 | 30 |
| Organic granulating solvent (example, alcohol)* | — | — | — | q.s |
| % release in 30 mins | <30 | <85 | <85 | <85 |
| % release in 120 mins | <35 | >45 | >35 | >35 |

*removed during drying process.

It should be noted that the compositions of Examples 6 to 9 can be formulated to enable tablet dosage form with the inclusion of appropriate tabletting aids such as binder, disintegrant, lubricants etc.

Unlike Example 1 and 6, the calculated drug release profile of Examples 7, 8 and 9 shown in Table II, illustrate the advantages of the carrier for testosterone undecanoate of varied particle size or through organic solvent granulation.

Example 10—Testosterone Undecanoate Coated Tablets

Testosterone undecanoate tablets of Example 6 through 9 can be further coated with a coating solution having typical composition set forth in Table III, using the conventional tablet coating procedures known in the art to a weight gain of about 3.0%.

TABLE III

| Ingredients | Composition in % w/w |
|---|---|
| Hypromellose (Methocel E 5) | 8.0 |
| Polyethylene glycol, NF 8000 | 0.6 |

TABLE III-continued

| Ingredients | Composition in % w/w |
|---|---|
| Isopropyl alcohol, USP | 54.8 |
| Water | 36.6 |

Examples 11-15—Testosterone Undecanoate Composition

Testosterone undecanoate formulations of Examples 11-15 were prepared by using the components set forth in Table IV and the method similar to that described for Examples 2-5. Each of the formulations was tested for release of the testosterone undecanoate using a USP Type II apparatus in 1000 mL of 8 wt % Triton X-100 in water at 37° C. and 100 rpm. The percent of the testosterone undecanoate released from each formulation was analyzed using HPLC. The release profiles are also shown in Table IV.

TABLE IV

| | Composition % w/w | | | | |
|---|---|---|---|---|---|
| Ingredients | Example 11 | Example 12 | Example 13 | Example 14 | Example 15 |
| Testosterone Undecanoate | 14 | 14 | 15 | 22 | 25 |
| Oleic acid | 75 | — | — | — | — |
| Lipophilic additive: Glyceryl Monolinoleate, NF | — | 68 | 63 | — | — |
| Hydrophilic additive: Polyoxyl 40 Hydrogenated Castor Oil, NF | — | 7 | 11 | — | — |

TABLE IV-continued

|  | Composition % w/w | | | | |
| --- | --- | --- | --- | --- | --- |
| Ingredients | Example 11 | Example 12 | Example 13 | Example 14 | Example 15 |
| Polyoxyl 35 Castor Oil, NF (Cremophor ® EL) | — | — | — | — | 21 |
| Glyceryl Palmitostearate (Glyceryl distearate GDS, Precirol ATO 5) | — | — | 5 | — | — |
| Tocopherol Polyethylene Glycol Succinate, NF | — | — | — | 22 | — |
| Vitamin E, USP (d,1-α-tocopherol) | — | — | — | 34 | 48 |
| Hydrophilic additive: Polyethylene Glycol 8000, USP | 11 | 11 | 6 | 4 | 6 |
| Hypromellose (100,000 cPs) | — | — | — | 18 | — |
| % release in 30 mins | 69 | 61 | 34 | 11 | 32 |
| % release in 120 mins | 100 | 100 | 88 | 48 | 99 |

Example 16—Testosterone Undecanoate Tablets

Testosterone undecanoate containing granules for tableting having the components set forth in Table V can be prepared by wet granulation methods. Accordingly, testosterone undecanoate, microcrystalline cellulose and croscarmellose sodium are passed through an ASTM mesh #40 mesh sieve and mixed in a low shear granulator to form a uniform blend. A binder solution of Starch 1500 in deionized water can be used to granulate the dry powder blend to a typical granulation end-point. The wet granulate dried using a tray dryer or fluid air dryer can be passed through a sized/screened, lubricated with Aerosil 200 and magnesium stearate, and compressed into tablets.

TABLE V

| Ingredients | Composition in % w/w |
| --- | --- |
| Testosterone Undecanoate | 28 |
| Microcrystalline Cellulose (Avicel PH 102) | 52.5 |
| Cro scarmello se sodium | 10 |
| Pregelatineized starch (Starch 1500) | 8 |
| Colloidal silicon dioxide (Aerosil 200) | 0.5 |
| Magnesium stearate | 1 |

The tablets of Example 16 exhibit about 30% testosterone undecanoate release in the first 120 minutes when tested using a USP Type II apparatus in 1000 mL of 8 wt % Triton X-100 in water at 37° C. and 100 rpm.

Examples 17-22—Testosterone Undecanoate Compositions

Testosterone undecanoate formulations of Table VI are free of lipid substances. Examples 17,18 and 19 were prepared by using the components set forth in Table VI and according to the following method: The Testosterone Undecanoate was dissolved in ethanol along with the correspondingly indicated hydrophilic additives. The clear solution so obtained was then slowly poured on microcrystalline cellulose under low-shear mixing. The granules were dried under a gentle current of air at room temperature. The dried granules were passed through ASTM #40 mesh. A predetermined weight of the resulting granules was filled into appropriate size capsules according to the testosterone undecanoate dose required.

Testosterone undecanoate formulations of Examples 20, 21 and 22 can be prepared by using the components set forth in Table VI and according to the following method: The required quantities of the respective inactive component and the testosterone undecanoate, were taken in a clean stainless steel container and mixed gently at about 50° C. to 70° C. using a stirrer, to get a clear-to-hazy liquid mixture. A predetermined weight of the resulting liquid mixture is disposed into hard gelatin capsule and allowed to solidify at room temperature.

The dosage forms of each Example 17-22 were tested for release of the testosterone undecanoate using a USP Type II apparatus in 1000 mL of 8 wt % Triton X-100 in water at 37° C. and 100 rpm. The percent of the testosterone undecanoate released from each formulation was analyzed using HPLC. The results of the release testing are also shown in Table VI. It should be noted that the compositions of Examples 17-22 can be formulated to enable tablet dosage form with the inclusion of appropriate tabletting aids such as diluents, binder, disintegrant, lubricants etc.

TABLE VI

|  | Composition in % w/w | | | | | |
| --- | --- | --- | --- | --- | --- | --- |
| Ingredients | Example 17 | Example 18 | Example 19 | Example 20 | Example 21 | Example 22 |
| Testosterone Undecanoate | 45 | 40 | 40 | 91 | 34 | 60 |
| Hydrophilic additive: (ex. PEG 8000 USP) | — | — | — | 7 | 30 | 40 |
| Hydrophilic additive: Sodium Lauryl sulfate | 10 | 9 | 9 | — | — | — |
| Microcrystalline Cellulose*, | 45 | 40 | 39 | — | — | — |
| Hydrophilic additive: (ex.Pluronic F 68) | 0 | 11 | 11 | — | — | — |
| Hydrophilic additive: (ex.Polyvinylpyrrolidone (Povidone K 30)) | 0 | 0 | 1 | 2 | 36 | — |
| % release in 30 mins | 19 | 23 | 24 | 19 | 17 | 18 |
| % release in 120 mins | 52 | 56 | 59 | 48 | 60 | 59 |

*Magnesium alumnometasilicate (Neuslin ®), lactose and other similar substances can be used The in vitro testosterone undecanoate release profiles of Examples 17 to 22 could be seen to be superior over the release profile of the Example 16.

Examples 23-27—Testosterone Undecanoate Compositions

Testosterone undecanoate formulations of Examples 23-27 were prepared by using the components set forth in Table VII. Each of the formulations was prepared by melting the testosterone undecanoate together with the corresponding inactive component in a stainless steel container at about 50° C. to 70° C. with gentle stirring to get a clear-to hazy liquid mixture. A predetermined weight of the resulting liquid mixture is disposed into hard gelatin capsule and allowed to solidify at room temperature. It should be noted that the liquid mixture can also be allowed to solidify to room temperature to get solid aggregates which may be sized through a ASTM mesh #30 to get granular particulates, which can be further filled in hard gelatin capsules.

Each of the formulations was tested for release of the testosterone undecanoate using a USP Type II apparatus in 1000 mL of 8 wt % Triton X-100 in water at 37° C. and 100 rpm. The percent of the testosterone undecanoate released from each formulation was analyzed using HPLC. The results of the release testing are also shown in Table VII.

TABLE VII

| Ingredients | Composition in % w/w | | | | |
|---|---|---|---|---|---|
| | Example 23 | Example 24 | Example 25 | Example 26 | Example 27 |
| Testosterone Undecanoate | 91 | 50 | 25 | 20 | 85 |
| Hydrophilic additive: (e.g. Povidone K 17) | 9 | 50 | 75 | — | — |
| Lipophilic additive: (e.g. Glycerol esters of $C_{12}$-$C_{18}$ fatty acids) | — | — | — | 80 | 15 |
| % release in 30 mins | 12 | 20 | 15 | 35 | 16 |
| % release in 120 mins | 32 | 50 | 65 | 48 | 43 |

Example 28—Testosterone Undecanoate Spray Dried Multiparticulates

Testosterone undecanoate multiparticulates can be prepared as follows: 15 g of a milled testosterone undecanoate and lactose, mixture (95:5 w/w), are passed through ASTM mesh #60 sieve and added under mixing to about 250 mL solution of, 8% w/v povidone K17 in water The resulting suspension can be spray dried using a conventional spray drying equipment with settings, for example, at heat inlet temperature of about 60-75° C. and an outlet temperature of about 30-38° C., aspirator set at 90-100%, the pump set at about 8-12 mL/min, and the flow rate set at about 500-600 L/hr. The final solid multiparticulate testosterone undecanoate composition can have a compositional makeup of about 53 wt % testosterone undecanoate, about 2.8 wt % lactose and about 44.2 wt % povidone K17.

Example 29—Testosterone Undecanoate Cyclodextrin Complexes

Testosterone undecanoate cyclodextrin complexes can be prepared by co-precipitation methods using various molar ratios of 1:1, 2:1, 3:1, and 1:2 of the testosterone undecanoate to beta-cyclodextrin, respectively. A significantly increased release rate of testosterone undecanoate can be achieved with the cyclodextrins complexes in an in vitro release testing in about 1000 mL of a 8% w/w Triton X-100 solution at 37° C. in a USP-2 apparatus set at 100 rpm, when compared to the free form of the drug. Granulates of the cyclodextrin/testosterone undecanoate complex can be made using the standard granulation or pelleting techniques using additional conventional pharmaceutical processing aids known in the art.

Example 30-34—Testosterone Undecanoate Compositions

A mixture of testosterone undecanoate and the corresponding formulation components can be melted together to get thermosetting fill to be disposed into capsule. Alternatively, the mixture can be fed into a melt-extruder apparatus for example, a single-screw extruder (Killion, Model KLB 100) equipped with about 1 inch diameter screw and about 6 inch flex lip die, and the die opening adjusted to about 0.005 inches and the screw speed was set at about 50 rpm. The residence time of the materials within the extruder can be set for about 2 to 8 minutes. The extruded strands can be cooled to room temperature by passing over a chilled roll. The strands can then be sized through an ASTM mesh #40 and the powder disposed into capsules. The exemplary formulations for melt-extrusion are indicated in Table VIII. These dosage forms can release 35% or more testosterone undecanoate in about first 120 minutes and about 85% or less in the first 30 minutes.

It should be noted that the testosterone undecanoate compositions of Table VIII can be further formulated to include one or more of other substances such as lactose, starches, hydroxypropyl methyl cellulose, methacrylate etc., at varying concentrations from about 12% to about 88% by weight of the total composition either prior to melt-extrusion or after sizing the melt-extruded composition, in order to prepare solid multi-particulates for tablets.

TABLE VIII

| Ingredients | Composition in % w/w | | | | |
|---|---|---|---|---|---|
| | Example 30 | Example 31 | Example 32 | Example 33 | Example 34 |
| Testosterone Undecanoate | 70 | 40 | 50 | 80 | 60 |
| Polyethylene glycol 8000 USP | 10 | — | 20 | 15 | 20 |
| (Glyceryl distearate GDS, Precirol ATO 5) | 10 | 40 | 20 | — | — |
| Stearic acid | 10 | 20 | 10 | — | — |
| Cholesterol | — | — | — | 5 | 20 |

Example 35—Testosterone Undecanoate Compositions Produced by Co-Milling

A testosterone undecanoate containing composition can be prepared by co-milling (co-grinding) 80 g solid testosterone undecanoate along with 15 g PVP K 17 and 5 g of sodium lauryl sulphate for a period from about 12 hours to about 24 hours using a ceramic ball-mill maintained at about 20±5° C. The co-milled composition can provide a superior in vitro drug release profile which could be at least 20% more when compared to the in vitro release profile of Example 1 when tested using a USP Type II apparatus in 1000 mL of 8 wt % Triton X-100 in water at 37° C. and 100 rpm.

Example 36—Testosterone Undecanoate Loaded Pellets

Testosterone undecanoate coated pellets were prepared using the ingredients set forth in Table IX. A spraying solution of the coating materials can be prepared by dissolving 25 g of testosterone undecanoate, 6 g of Pluronic F 68 and 5 g of PVP K 30 in about 250 mL of dehydrated alcohol. The spray solution can be intermittently sprayed on to a rolling bed of 64 g commercially available microcrystalline cellulose spheres (for example, having a mean particle size in the range of about 250 µm to about 600 µm) taken in a convention coating pan. After all the spray solution is loaded on the spheres, it can be dried under gentle current of air for at least 1 hour to remove the solvent. Thus, by adjusting the pan speed, spray rate and the inlet air flow and temperature, the testosterone undecanoate loaded pellets or beads can be obtained which can be disposed into a capsule. Auxiliary pharmaceutical process aids such as talc, starch etc. may be dusted during the spraying process to avoid agglomeration of the pellets.

It should be noted that appropriate similar or equivalent equipment known in the art may be used for the purpose. Also, by varying the quantity of spray solution sprayed on the spheres or by varying the concentration of testosterone undecanoate in the spray solution, pellets of different drug loading can be achieved.

TABLE IX

| Ingredients | Composition in % w/w |
| --- | --- |
| Testosterone Undecanoate | 25 |
| Pluronic F 68 | 6 |
| Polyvinylpyrrolidone K 30 | 5 |
| Dehydrated Alcohol | 250 mL |
| microcrystalline cellulose spheres (Celsphere) | 64 |

Example 37—Testosterone Undecanoate Composition with Hydrophilic Additive

Enhancement of the release rate of testosterone undecanoate can be achieved by eutectic or non-eutectic mixtures with a hydrophilic additive such as polyethylene glycol (PEG), particularly PEG having molecular weights of about 1000 or more. For example, about 1 g of testosterone undecanoate can be combined with 0.3 g of PEG (molecular weight 8000) and 0.5 g of Poloxamer (Pluronic F68). The mixture can be melted at about 60° C.-70° C. under stirring and then subsequently solidified to room temperature. The resulting solid can be sized through an ASTM mesh #30 and filled into capsule or pressed into a tablet. It should be noted that pharmaceutical aids such as diluents, disintegrates and/or lubricants can be optionally used to get the tablets or capsules.

Example 38—Testosterone Undecanoate Compositions with Lipophilic Additive

Enhancement of the release rate of testosterone undecanoate can be achieved by eutectic or non-eutectic mixtures with a lipophilic additive such as hydrogenated castor oil, glyceryl palmitostearate, glyceryl distearate, stearic acid etc. For example, about 10 g of testosterone undecanoate can be combined with 0.5 g of glyceryl palmitostearate (Precirol® ATO 5) and 1 g of stearic acid. The mixture can be melted at about 60° C.-70° C. under stirring and allowed to solidify at room temperature. The resulting solid can be sized through an ASTM mesh #30 and filled into capsule or pressed into a tablet. It should be noted that pharmaceutical aids such as diluents, disintegrates and/or lubricants can be optionally used to get the tablets or capsules.

Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

The invention claimed is:

1. A method for replacement therapy in males having a condition or a symptom associated with a deficiency or absence of endogenous testosterone, said method comprising orally administering, with food having 10 to 50 grams of fat, to males having a condition associated with a deficiency or absence of endogenous testosterone twice daily a tablet comprising 100 mg to 400 mg testosterone undecanoate and a pharmaceutically acceptable carrier including at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxyl propyl methyl cellulose; ethyl cellulose; carbomers; gelatin; poloxamers; sodium dodecyl sulfate; sodium docusate; polyoxyethylene sorbitan esters; glycerin; paraffin oil; silicone oils; magnesium aluminosilicates; silicon dioxide; ethyl alcohol; benzyl alcohol; benzyl benzoate; ascorbic acid; or mixtures thereof said method providing a serum testosterone mean Cavg in the range of 400 ng/dL to 600 ng/dL wherein said tablet releases at least 45% of the testosterone undecanoate at 120 minutes and less than 85% of the testosterone undecanoate at 30 minutes when tested, using a USP Type II apparatus, in 1000 mL of 8 wt % Triton X-100 at 37° C. and 100 rpm.

2. The method of claim 1 wherein the tablet is free of lipophilic surfactants.

3. The method of claim 1 wherein the tablet does not form an oil-in-water emulsion when contacted with water with adequate mixing.

4. The method of claim 1 wherein the testosterone undecanoate is present in solid particulate form in the tablet.

5. The method of claim 1 wherein 30% (w/w) or more of the testosterone undecanoate is present in solid particulate form in the tablet.

6. The method of claim 1 wherein the tablet includes 15% or less of lipid substance.

7. A method for replacement therapy in males having a condition associated with a deficiency or absence of endogenous testosterone, said method comprising orally administering, with food having 10 to 50 grams of fat, to males having a condition or a symptom associated with a deficiency or absence of endogenous testosterone twice daily a tablet comprising testosterone undecanoate and a pharmaceutically acceptable carrier including at least one of polyvinyl alcohol, polyvinyl pyrrolidones, polyethylene glycols having molecular weight from about 100 to about 20,000;

propylene glycol; starches; sodium starch glycolate; croscarmellose; sucrose; lactose; cyclodextrins; carboxymethyl cellulose; microcrystalline cellulose, hydroxyl propyl methyl cellulose; ethyl cellulose; carbomers; gelatin; poloxamers; sodium dodecyl sulfate; sodium docusate; polyoxyethylene sorbitan esters; glycerin; paraffin oil; silicone oils; magnesium aluminosilicates; silicon dioxide; ethyl alcohol; benzyl alcohol; benzyl benzoate; ascorbic acid; or mixtures thereof, wherein testosterone undecanoate is at least 30% (w/w) solid particulate testosterone undecanoate said method providing a serum testosterone mean Cavg in the range of 400 ng/dL to 600 ng/dL wherein said tablet releases at least 45% of the testosterone undecanoate at 120 minutes and less than 85% of the testosterone undecanoate at 30 minutes when tested, using a USP Type II apparatus, in 1000 mL of 8 wt % Triton X-100 at 37° C. and 100 rpm.

8. The method of claim 7 wherein the tablet is free of lipophilic surfactants.

9. The method of claim 7 wherein the tablet does not form an oil-in-water emulsion when contacted with water with adequate mixing.

10. The method of claim 7 wherein the testosterone undecanoate is present in solid particulate form in the tablet.

11. The method of claim 7 wherein 70% (w/w) or more of the testosterone undecanoate is present in solid particulate form in solid particulate form.

12. The method of claim 7 wherein the tablet includes 15% or less of lipid substance.

13. The method of claim 7 wherein the tablet has from about 100 mg to about 400 mg testosterone undecanoate.

14. A method for replacement therapy in males having a condition or a symptom associated with a deficiency or absence of endogenous testosterone, said method comprising orally administering, with food having 10 to 50 grams of fat, to males having a condition associated with a deficiency or absence of endogenous testosterone twice daily a tablet comprising testosterone undecanoate and a pharmaceutically acceptable carrier including at least one of polyvinyl alcohol, polyvinyl pyrrolidones, polyethylene glycols having molecular weight from about 100 to about 20,000; propylene glycol; starches; sodium starch glycolate; croscarmellose; sucrose; lactose; cyclodextrins; carboxymethyl cellulose; microcrystalline cellulose, hydroxyl propyl methyl cellulose; ethyl cellulose; carbomers; gelatin; poloxamers; sodium dodecyl sulfate; sodium docusate; polyoxyethylene sorbitan esters; glycerin; paraffin oil; silicone oils; magnesium aluminosilicates; silicon dioxide; ethyl alcohol; benzyl alcohol; benzyl benzoate; ascorbic acid; or mixtures thereof wherein said tablet comprises 100 mg to 400 mg of testosterone undecanoate and said method providing a mean Cavg in the range of 400 ng/dL to 600 ng/dL, wherein said tablet releases at least 45% of the testosterone undecanoate at 120 minutes and less than 85% of the testosterone undecanoate at 30 minutes when tested, using a USP Type II apparatus, in 1000 mL of 8 wt % Triton X-100 at 37° C. and 100 rpm.

15. The method of claim 14 wherein the tablet includes 15% or less of lipid substance.

16. The method of claim 14 wherein 30% (w/w) or more of the testosterone undecanoate is present in solid particulate form in the tablet.

17. The method of claim 14 wherein the tablet does not form an oil-in-water emulsion when contacted with water with adequate mixing.

18. The method of claim 7 wherein the tablet has an amount of testosterone undecanoate to pharmaceutically acceptable carrier ratio of from about 2:1 (w/w) to about 1:2 (w/w).

19. The method of claim 1 wherein the testosterone undecanoate is micronized or has a mean particle diameter of 50 μm or less.

20. The method of claim 7 wherein the testosterone undecanoate is micronized or has a mean particle diameter of 50 μm or less.

21. The method of claim 14 wherein the testosterone undecanoate is micronized or has a mean particle diameter of 50 μm or less.

* * * * *